United States Patent
Drake et al.

(10) Patent No.: US 10,463,853 B2
(45) Date of Patent: Nov. 5, 2019

(54) INTERVENTIONAL MEDICAL SYSTEMS

(71) Applicant: Medtronic, Inc., Minneapolis, MN (US)

(72) Inventors: Ronald A Drake, St. Louis Park, MN (US); Xin Chen, Circle Pines, MN (US); Michael D Eggen, Chisago City, MN (US); Matthew D Bonner, Plymouth, MN (US); Vladimir Grubac, Brooklyn Park, MN (US); Brian P Colin, Shakopee, MN (US); Kenneth C Gardeski, Plymouth, MN (US); Kevin R Seifert, Forest Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 169 days.

(21) Appl. No.: 15/410,085

(22) Filed: Jan. 19, 2017

(65) Prior Publication Data

US 2017/0209688 A1    Jul. 27, 2017

Related U.S. Application Data

(60) Provisional application No. 62/281,312, filed on Jan. 21, 2016.

(51) Int. Cl.
*A61N 1/05* (2006.01)
*A61N 1/368* (2006.01)
(Continued)

(52) U.S. Cl.
CPC .......... *A61N 1/0573* (2013.01); *A61B 5/6882* (2013.01); *A61N 1/057* (2013.01);
(Continued)

(58) Field of Classification Search
CPC ..... A61N 1/0573; A61N 1/057; A61B 5/6882
(Continued)

(56) References Cited

U.S. PATENT DOCUMENTS

| 721,869 A | 3/1903 | Dunning |
|---|---|---|
| 3,717,151 A | 2/1973 | Collett |

(Continued)

FOREIGN PATENT DOCUMENTS

| CA | 1003904 A1 | 1/1977 |
|---|---|---|
| CN | 1882370 | 12/2006 |

(Continued)

OTHER PUBLICATIONS http://www.mana-tech.com/factsheets/HomerMammalok.pdf.
(Continued)

*Primary Examiner* — Amanda K Hulbert
*Assistant Examiner* — Philip C Edwards
(74) *Attorney, Agent, or Firm* — Shumaker & Sieffert, P.A.

(57) ABSTRACT

An implantable medical device includes ventricular and atrial portions, and a flexible leadlet that extends therebetween. An open channel of the atrial portion, formed along a core thereof, is sized to receive the leadlet therein, when the leadlet is folded over on itself. An interventional medical system includes the device and a delivery tool; a tubular sidewall of the tool defines a lumen and has a tether extending therein. A slot formed in the sidewall extends proximally from an open end thereof, coincident with a distal opening of the lumen. When the atrial portion is contained within the lumen, a segment of the leadlet extends alongside the atrial portion; another segment of the leadlet, being folded over on itself, proximal to the atrial portion, has the tether engaged therewith. The slot may allow passage of (Continued)

the leadlet therethrough, when the atrial portion is positioned for deployment through the distal opening.

12 Claims, 21 Drawing Sheets

(51) Int. Cl.
*A61B 5/00* (2006.01)
*A61N 1/375* (2006.01)
*A61N 1/362* (2006.01)
*A61N 1/372* (2006.01)

(52) U.S. Cl.
CPC ......... *A61N 1/3622* (2013.01); *A61N 1/3684* (2013.01); *A61N 1/3688* (2013.01); *A61N 1/3756* (2013.01); *A61N 1/37205* (2013.01); *A61N 2001/058* (2013.01)

(58) Field of Classification Search
USPC ......................................................... 607/123
See application file for complete search history.

(56) References Cited

U.S. PATENT DOCUMENTS

| | | |
|---|---|---|
| 3,754,555 A | 8/1973 | Schmitt |
| 3,814,104 A | 6/1974 | Irnich et al. |
| 3,835,864 A | 9/1974 | Rasor et al. |
| 3,902,501 A | 9/1975 | Citron et al. |
| 3,943,936 A | 3/1976 | Rasor |
| 3,971,364 A | 7/1976 | Fletcher et al. |
| 3,976,082 A | 8/1976 | Schmitt |
| 4,103,690 A | 8/1978 | Harris |
| 4,112,952 A | 9/1978 | Thomas et al. |
| 4,269,198 A | 5/1981 | Stokes |
| 4,280,512 A | 7/1981 | Karr |
| 4,301,815 A | 11/1981 | Doring |
| 4,402,328 A | 9/1983 | Doring |
| 4,409,994 A | 10/1983 | Doring |
| 4,502,492 A | 3/1985 | Bornzin |
| 4,662,382 A | 5/1987 | Sluetz et al. |
| 4,898,577 A | 2/1990 | Badger et al. |
| 4,913,164 A | 4/1990 | Greene et al. |
| 5,003,990 A | 4/1991 | Osypka |
| 5,057,114 A | 10/1991 | Wittich et al. |
| 5,129,749 A | 7/1992 | Sato |
| 5,171,233 A | 12/1992 | Amplatz et al. |
| 5,193,540 A | 3/1993 | Schulman et al. |
| 5,257,634 A | 11/1993 | Kroll |
| 5,282,845 A | 2/1994 | Bush et al. |
| 5,300,107 A | 4/1994 | Stokes et al. |
| 5,318,528 A | 6/1994 | Heaven et al. |
| 5,336,253 A | 8/1994 | Gordon et al. |
| 5,405,367 A | 4/1995 | Schulman et al. |
| 5,405,374 A | 4/1995 | Stein |
| 5,411,535 A | 5/1995 | Fujii et al. |
| 5,425,756 A | 6/1995 | Heil et al. |
| 5,443,492 A | 8/1995 | Stokes et al. |
| 5,492,119 A | 2/1996 | Abrams |
| 5,522,875 A | 6/1996 | Gates et al. |
| 5,522,876 A | 6/1996 | Rusink |
| 5,545,201 A | 8/1996 | Helland et al. |
| 5,545,206 A | 8/1996 | Carson |
| 5,562,723 A | 10/1996 | Rugland et al. |
| 5,575,814 A | 11/1996 | Giele et al. |
| 5,578,068 A | 11/1996 | Laske et al. |
| 5,697,936 A | 12/1997 | Shipko et al. |
| 5,716,390 A | 2/1998 | Li |
| 5,716,391 A | 2/1998 | Grandjean |
| 5,755,764 A | 5/1998 | Schroeppel |
| 5,776,178 A | 7/1998 | Pohndorf et al. |
| 5,807,399 A | 9/1998 | Laske et al. |
| 5,837,006 A | 11/1998 | Ocel et al. |
| 5,837,007 A | 11/1998 | Altman et al. |
| 5,851,226 A | 12/1998 | Skubitz et al. |
| 5,871,531 A | 2/1999 | Struble |
| 5,908,381 A | 6/1999 | Aznoian et al. |
| 5,908,447 A | 6/1999 | Schroeppel et al. |
| 6,041,258 A | 3/2000 | Cigaina et al. |
| 6,055,457 A | 4/2000 | Bonner |
| 6,074,401 A | 6/2000 | Gardnier et al. |
| 6,078,840 A | 6/2000 | Stokes |
| 6,093,177 A | 7/2000 | Javier et al. |
| 6,129,749 A | 10/2000 | Bartig et al. |
| 6,132,456 A | 10/2000 | Sommer et al. |
| 6,181,973 B1 | 1/2001 | Ceron et al. |
| 6,188,932 B1 | 2/2001 | Lindegren |
| 6,240,322 B1 | 5/2001 | Peterfeso et al. |
| 6,251,104 B1 | 6/2001 | Kesten et al. |
| 6,290,719 B1 | 9/2001 | Garberoglio |
| 6,321,124 B1 | 11/2001 | Cigaina |
| 6,322,548 B1 | 11/2001 | Payne et al. |
| RE37,463 E | 12/2001 | Altman |
| 6,358,256 B1 | 3/2002 | Reinhardt |
| 6,363,938 B2 | 4/2002 | Saadat et al. |
| 6,381,495 B1 | 4/2002 | Jenkins |
| 6,381,500 B1 | 4/2002 | Fischer, Sr. |
| 6,408,214 B1 | 6/2002 | Williams et al. |
| 6,458,145 B1 | 10/2002 | Ravenscroft et al. |
| 6,477,423 B1 | 11/2002 | Jenkins |
| 6,500,182 B2 | 12/2002 | Foster |
| 6,510,332 B1 | 1/2003 | Greenstein |
| 6,510,345 B1 | 1/2003 | Van Bentem |
| 6,522,915 B1 | 2/2003 | Ceballos et al. |
| 6,572,587 B2 | 6/2003 | Lerman et al. |
| 6,582,441 B1 | 6/2003 | He et al. |
| 6,592,581 B2 | 7/2003 | Bowe |
| 6,623,518 B2 | 9/2003 | Thompson et al. |
| 6,626,915 B2 | 9/2003 | Leveillee |
| 6,638,268 B2 | 10/2003 | Niazi |
| 6,684,109 B1 | 1/2004 | Osypka |
| 6,711,443 B2 | 3/2004 | Osypka |
| 6,738,672 B2 | 5/2004 | Schulman et al. |
| 6,743,240 B2 | 6/2004 | Smith et al. |
| 6,755,812 B2 | 6/2004 | Peterson et al. |
| 6,823,217 B2 | 11/2004 | Rutten et al. |
| 6,909,920 B2 | 6/2005 | Lokhoff et al. |
| 6,944,507 B2 | 9/2005 | Froberg |
| 6,953,454 B2 | 10/2005 | Peterson et al. |
| 7,027,876 B2 | 4/2006 | Casavant et al. |
| 7,082,335 B2 | 7/2006 | Klein et al. |
| 7,082,336 B2 | 7/2006 | Ransbury et al. |
| 7,085,606 B2 | 8/2006 | Flach et al. |
| 7,092,765 B2 | 8/2006 | Geske et al. |
| 7,092,766 B1 | 8/2006 | Salys et al. |
| 7,120,504 B2 | 10/2006 | Osypka |
| 7,130,700 B2 | 10/2006 | Gardeski et al. |
| 7,149,587 B2 | 12/2006 | Wardle et al. |
| 7,158,838 B2 | 1/2007 | Seifert et al. |
| 7,162,310 B2 | 1/2007 | Doan |
| 7,181,288 B1 | 2/2007 | Rezai et al. |
| 7,187,982 B2 | 3/2007 | Seifert et al. |
| 7,200,437 B1 | 4/2007 | Nabutovsky et al. |
| 7,212,869 B2 | 5/2007 | Wahlstrom et al. |
| 7,229,415 B2 | 6/2007 | Schwartz |
| 7,251,532 B2 | 7/2007 | Hess et al. |
| 7,289,853 B1 | 10/2007 | Campbell et al. |
| 7,313,445 B2 | 12/2007 | McVenes et al. |
| 7,326,231 B2 | 2/2008 | Phillips et al. |
| 7,328,071 B1 | 2/2008 | Stehr et al. |
| 7,331,922 B2 | 2/2008 | Mohl |
| 7,383,091 B1 | 6/2008 | Chitre et al. |
| 7,450,999 B1 | 11/2008 | Karicherla et al. |
| 7,462,184 B2 | 12/2008 | Worley et al. |
| 7,463,933 B2 | 12/2008 | Wahlstrom et al. |
| 7,499,758 B2 | 3/2009 | Cates et al. |
| 7,509,169 B2 | 3/2009 | Eigler et al. |
| 7,515,971 B1 | 4/2009 | Doan |
| 7,532,939 B2 | 5/2009 | Sommer et al. |
| 7,558,631 B2 | 7/2009 | Cowan et al. |
| 7,634,319 B2 | 12/2009 | Schneider et al. |
| 7,647,109 B2 | 1/2010 | Hastings et al. |
| 7,657,325 B2 | 2/2010 | Williams |

(56) References Cited

U.S. PATENT DOCUMENTS

| | | |
|---|---|---|
| 7,678,128 B2 | 3/2010 | Boyle et al. |
| 7,717,899 B2 | 5/2010 | Bowe et al. |
| 7,731,655 B2 | 6/2010 | Smith et al. |
| 7,734,343 B2 | 6/2010 | Ransbury et al. |
| 7,740,640 B2 | 6/2010 | Ginn |
| 7,785,264 B2 | 8/2010 | Hettrick et al. |
| 7,799,037 B1 | 9/2010 | He et al. |
| 7,801,624 B1 | 9/2010 | Flannery et al. |
| 7,835,801 B1 | 11/2010 | Sundararajan et al. |
| 7,840,281 B2 | 11/2010 | Kveen et al. |
| 7,840,283 B1 | 11/2010 | Bush et al. |
| 7,860,580 B2 | 12/2010 | Falk et al. |
| 7,875,049 B2 | 1/2011 | Eversull et al. |
| 7,890,186 B2 | 2/2011 | Wardle et al. |
| 7,904,179 B2 | 3/2011 | Rutten et al. |
| 7,920,928 B1 | 4/2011 | Yang et al. |
| 7,949,395 B2 | 5/2011 | Kuzma |
| 7,993,351 B2 | 8/2011 | Worley et al. |
| 8,010,209 B2 | 8/2011 | Jacobson |
| 8,012,127 B2 | 9/2011 | Lieberman et al. |
| 8,032,219 B2 | 10/2011 | Neumann et al. |
| 8,036,757 B2 | 10/2011 | Worley |
| 8,057,486 B2 | 11/2011 | Hansen |
| 8,082,035 B2 | 12/2011 | Glukhovsky |
| 8,103,361 B2 | 1/2012 | Moser |
| 8,108,054 B2 | 1/2012 | Helland |
| 8,142,347 B2 | 3/2012 | Griego et al. |
| 8,160,722 B2 | 4/2012 | Rutten et al. |
| 8,170,690 B2 | 5/2012 | Morgan et al. |
| 8,185,213 B2 | 5/2012 | Kveen et al. |
| 8,219,213 B2 | 7/2012 | Sommer et al. |
| 8,233,994 B2 | 7/2012 | Sommer et al. |
| 8,252,019 B2 | 8/2012 | Fleming, III |
| 8,262,672 B2 | 9/2012 | Neidert et al. |
| 8,295,939 B2 | 10/2012 | Jacobson |
| 8,313,445 B2 | 11/2012 | Mishima et al. |
| 8,352,025 B2 | 1/2013 | Jacobson |
| 8,352,028 B2 | 1/2013 | Wenger |
| 8,364,277 B2 | 1/2013 | Glukhovsky |
| 8,364,280 B2 | 1/2013 | Marnfeldt et al. |
| 8,406,900 B2 | 3/2013 | Barlov et al. |
| 8,406,901 B2 | 3/2013 | Starkebaum et al. |
| 8,418,362 B2 | 4/2013 | Zerfas et al. |
| 8,428,750 B2 | 4/2013 | Kolberg |
| 8,452,420 B2 | 5/2013 | Flach et al. |
| 8,478,431 B2 | 7/2013 | Griswold et al. |
| 8,489,189 B2 | 7/2013 | Tronnes |
| 8,494,650 B2 | 7/2013 | Glukhovsky et al. |
| 8,504,156 B2 | 8/2013 | Bonner et al. |
| 8,518,060 B2 | 8/2013 | Jelich et al. |
| 8,527,068 B2 | 9/2013 | Ostroff |
| 8,532,790 B2 | 9/2013 | Griswold |
| 8,548,605 B2 | 10/2013 | Ollivier |
| 8,565,897 B2 | 10/2013 | Regnier et al. |
| 8,615,310 B2 | 12/2013 | Khairkhahan et al. |
| 8,634,912 B2 | 1/2014 | Bornzin et al. |
| 8,670,842 B1 | 3/2014 | Bornzin et al. |
| 8,700,181 B2 | 4/2014 | Bornzin et al. |
| 8,721,587 B2 | 5/2014 | Berthiaume et al. |
| 8,727,996 B2 | 5/2014 | Allan et al. |
| 8,738,147 B2 | 5/2014 | Hastings et al. |
| 8,755,909 B2 | 6/2014 | Sommer et al. |
| 8,758,365 B2 | 6/2014 | Bonner et al. |
| 9,119,959 B2 | 9/2015 | Rys et al. |
| 9,155,882 B2 | 10/2015 | Grubac et al. |
| 9,414,857 B2 | 8/2016 | Wood et al. |
| 9,446,248 B2 | 9/2016 | Sheldon et al. |
| 9,526,891 B2 | 12/2016 | Eggen et al. |
| 9,539,423 B2 | 1/2017 | Bonner et al. |
| 10,071,243 B2 | 9/2018 | Kuhn et al. |
| 10,099,050 B2 | 10/2018 | Chen et al. |
| 2002/0077556 A1 | 6/2002 | Schwartz |
| 2002/0095203 A1 | 7/2002 | Thompson et al. |
| 2003/0004537 A1 | 1/2003 | Boyle et al. |
| 2003/0233139 A1* | 12/2003 | Chitre ................ A61N 1/0563 607/122 |
| 2004/0147973 A1 | 7/2004 | Hauser |
| 2004/0176797 A1 | 9/2004 | Opolski |
| 2004/0230280 A1 | 11/2004 | Cates |
| 2004/0249417 A1 | 12/2004 | Ransbury et al. |
| 2005/0090890 A1 | 4/2005 | Wu et al. |
| 2005/0267555 A1 | 12/2005 | Marnfeldt et al. |
| 2006/0085039 A1 | 4/2006 | Hastings et al. |
| 2006/0247753 A1 | 11/2006 | Wenger et al. |
| 2007/0043414 A1* | 2/2007 | Fifer ................ A61N 1/0565 607/126 |
| 2007/0135883 A1 | 6/2007 | Drasler et al. |
| 2007/0150037 A1 | 6/2007 | Hastings et al. |
| 2007/0150038 A1 | 6/2007 | Hastings et al. |
| 2007/0233218 A1 | 10/2007 | Kolberg |
| 2007/0239248 A1 | 10/2007 | Hastings et al. |
| 2007/0255376 A1 | 11/2007 | Michels et al. |
| 2007/0276444 A1 | 11/2007 | Gelbart |
| 2007/0293904 A1 | 12/2007 | Gelbart |
| 2008/0021532 A1 | 1/2008 | Kveen et al. |
| 2008/0051863 A1 | 2/2008 | Schneider |
| 2009/0082827 A1 | 3/2009 | Kveen et al. |
| 2009/0082828 A1 | 3/2009 | Ostroff |
| 2009/0204170 A1 | 8/2009 | Hastings et al. |
| 2009/0281605 A1 | 11/2009 | Marnfeldt et al. |
| 2010/0198288 A1 | 8/2010 | Ostroff |
| 2010/0211149 A1 | 8/2010 | Morgan et al. |
| 2011/0034939 A1 | 2/2011 | Kveen et al. |
| 2011/0054555 A1 | 3/2011 | Williams et al. |
| 2011/0112548 A1 | 5/2011 | Fifer et al. |
| 2011/0125163 A1 | 5/2011 | Rutten et al. |
| 2011/0190785 A1 | 8/2011 | Gerber et al. |
| 2011/0190786 A1 | 8/2011 | Gerber et al. |
| 2011/0208621 A1 | 8/2011 | Jacobson |
| 2011/0237967 A1 | 9/2011 | Moore et al. |
| 2011/0251660 A1* | 10/2011 | Griswold ........... A61N 1/37205 607/126 |
| 2011/0251661 A1 | 10/2011 | Fifer et al. |
| 2011/0251662 A1 | 10/2011 | Griswold et al. |
| 2011/0270339 A1 | 11/2011 | Murray, III et al. |
| 2011/0270340 A1 | 11/2011 | Pellegini et al. |
| 2011/0282423 A1 | 11/2011 | Jacobson |
| 2011/0307043 A1 | 12/2011 | Ollivier |
| 2012/0078322 A1 | 3/2012 | Dal Molin et al. |
| 2012/0078336 A1 | 3/2012 | Helland |
| 2012/0095539 A1 | 4/2012 | Khairkhahan et al. |
| 2012/0109002 A1 | 5/2012 | Mothilal et al. |
| 2012/0109079 A1 | 5/2012 | Asleson et al. |
| 2012/0109148 A1 | 5/2012 | Bonner et al. |
| 2012/0109149 A1 | 5/2012 | Bonner et al. |
| 2012/0116489 A1 | 5/2012 | Khairkhahan et al. |
| 2012/0158111 A1 | 6/2012 | Khairkhahan et al. |
| 2012/0165827 A1 | 6/2012 | Khairkhahan et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0197373 A1 | 8/2012 | Khairkhahan et al. |
| 2012/0232565 A1 | 9/2012 | Kveen et al. |
| 2012/0271134 A1 | 10/2012 | Allan et al. |
| 2012/0330392 A1 | 12/2012 | Regnier et al. |
| 2013/0006261 A1 | 1/2013 | Lampropoulos et al. |
| 2013/0006262 A1 | 1/2013 | Lampropoulos et al. |
| 2013/0012925 A1 | 1/2013 | Berthiaume et al. |
| 2013/0035636 A1 | 2/2013 | Beasley et al. |
| 2013/0035748 A1 | 2/2013 | Bonner et al. |
| 2013/0053921 A1 | 2/2013 | Bonner et al. |
| 2013/0079798 A1 | 3/2013 | Tran et al. |
| 2013/0079861 A1 | 3/2013 | Reinert et al. |
| 2013/0103047 A1 | 4/2013 | Steingisser et al. |
| 2013/0103049 A1 | 4/2013 | Bonde |
| 2013/0110127 A1 | 5/2013 | Bornzin et al. |
| 2013/0110219 A1 | 5/2013 | Bornzin et al. |
| 2013/0116738 A1 | 5/2013 | Samade et al. |
| 2013/0116740 A1 | 5/2013 | Bornzin et al. |
| 2013/0116741 A1 | 5/2013 | Bornzin et al. |
| 2013/0123875 A1 | 5/2013 | Varady et al. |
| 2013/0131591 A1 | 5/2013 | Berthiaume et al. |
| 2013/0131693 A1 | 5/2013 | Berthiaume et al. |

(56) References Cited

U.S. PATENT DOCUMENTS

| | | |
|---|---|---|
| 2013/0253342 A1 | 9/2013 | Griswold et al. |
| 2013/0253343 A1 | 9/2013 | Waldhauser et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0296957 A1 | 11/2013 | Tronnes |
| 2014/0058494 A1 | 2/2014 | Ostroff et al. |
| 2014/0074114 A1 | 3/2014 | Khairkhahan et al. |
| 2014/0107723 A1 | 4/2014 | Hou et al. |
| 2014/0148815 A1 | 5/2014 | Wenzel et al. |
| 2014/0180306 A1 | 6/2014 | Grubac et al. |
| 2015/0039069 A1 | 2/2015 | Rys et al. |
| 2015/0039070 A1 | 2/2015 | Kuhn et al. |
| 2015/0039071 A1 | 2/2015 | Grubac et al. |
| 2015/0051616 A1 | 2/2015 | Haasl et al. |
| 2015/0051682 A1 | 2/2015 | Schmidt et al. |
| 2015/0094668 A1 | 4/2015 | Wood et al. |
| 2015/0352353 A1 | 12/2015 | Rys et al. |
| 2016/0001068 A1 | 1/2016 | Grubac et al. |
| 2016/0059002 A1 | 3/2016 | Grubac et al. |

FOREIGN PATENT DOCUMENTS

| | | |
|---|---|---|
| DE | 2053919 A1 | 5/1972 |
| EP | 779080 B1 | 5/2003 |
| JP | H02-88666 | 7/1990 |
| JP | 05245215 A | 9/1993 |
| RU | 2011151104 | 6/2013 |
| WO | 2010131157 A1 | 7/1990 |
| WO | 03032807 A2 | 4/2003 |
| WO | 2004028348 A2 | 4/2004 |
| WO | 2009039400 A1 | 3/2009 |
| WO | 2009042295 A1 | 4/2009 |
| WO | 2012092067 A1 | 7/2012 |
| WO | 2012092074 A1 | 7/2012 |
| WO | 2014006471 A1 | 1/2014 |

OTHER PUBLICATIONS

Medtronic model SELECTSURE™ 3830 manual, 2013, 20 pages.
(PCT/US2017/014352) PCT Invitation to Pay Additional Fees and, Where Applicable, Protest Fee, dated Apr. 3, 2017, 7 pages.
(PCT/US2017/014361) PCT Notification of Transmittal of the International Search Report and the Written Opinion of the International Searching Authority, dated Apr. 3, 2017, 11 pages.
(PCT/US2017/014369) PCT Notification of Transmittal of the International Search Report and the Written Opinion of the International Searching Authority, dated May 10, 2017, 13 pages.
(PCT/US2017/014352) PCT Notification of Transmittal of the International Search Report and the Written Opinion of the International Searching Authority, or the Declaration, dated May 22, 2017, 8 pages.
International Search Report from Written Opinion from International Application No. PCT/US2014/047962, dated Feb. 5, 2015, 6 pp.
International Preliminary Report on Patentability from International Application No. PCT/US2014/047962, dated Feb. 2, 2016, 7 pp.
"Homer Mammalok Gold," accessed on or about Jan. 19, 2017, accessed from http://www.mana-tech.com/factsheets/HomerMammalok.pdf, 1 pp.
Merriam-Webster Definition of "Compound Curve," accessed on Apr. 25, 2017, https://merriam-webster.com/dictionary/compound%20curve, 4 pp.
Spickler, et al., "Totally Self-Contained Intracardiac Pacemaker," J. Electrocardiology, vol. 3, Nos. 3 & 4, pp. 325-331, 1970. (Applicant points out, in accordance with MPEP 609.04(a), that the year of publication, 1970 is sufficiently earlier than the effective U.S. filing date, so that the particular month of publication is not in issue.).
Prosecution History from U.S. Appl. No. 15/410,161, dated from Jan. 19, 2017 to Jun. 13, 2018, 31 pp.
Prosecution History from U.S. Appl. No. 16/158,724, dated from Oct. 12, 2018 to Nov. 29, 2018, 37 pp.
Prosecution History from U.S. Appl. No. 13/955,393, dated from Jul. 31, 2013 to Aug. 10, 2018, 71 pp.
Prosecution History from U.S. Appl. No. 16/128,270, dated from Sep. 11, 2018 to Apr. 29, 2019, 51 pp.
U.S. Appl. No. 16/128,270, filed by Jonathan L. Kuhn et al., filed on Sep. 11, 2018.
U.S. Appl. No. 16/158,724, filed by Xin Chen et al., filed on Oct. 12, 2018.
U.S. Appl. No. 15/410,161, filed by Xin Chen et al., filed on Jan. 19, 2017.
U.S. Appl. No. 13/955,393, filed by Jonathan L. Kuhn et al., filed on Jul. 31, 2013.
Response to Final Office Action dated Apr. 29, 2019, from U.S. Appl. No. 16/128,270, filed Jun. 24, 2019, 13 pp.
Notice of Allowance from U.S. Appl. No. 16/128,270, dated Aug. 21, 2019, 8 pp.

* cited by examiner

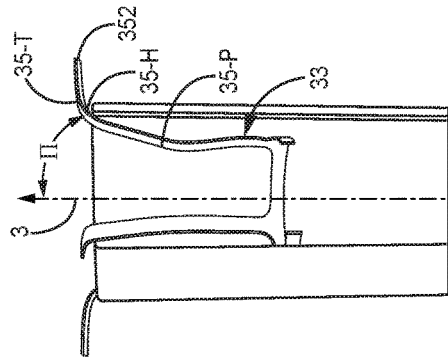
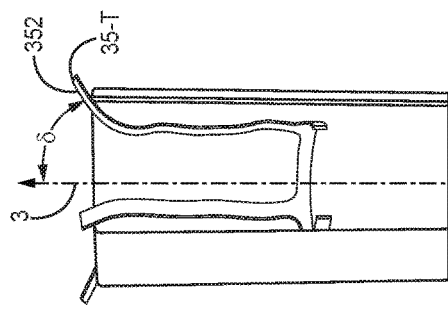
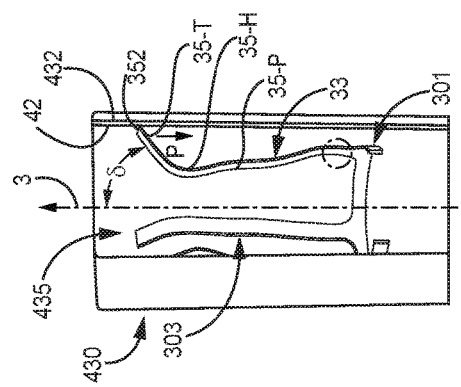
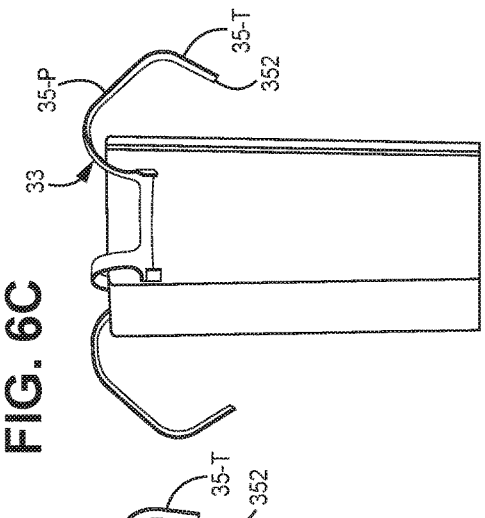
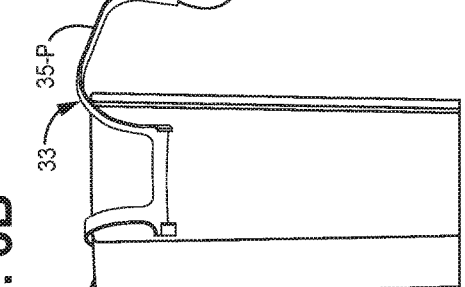
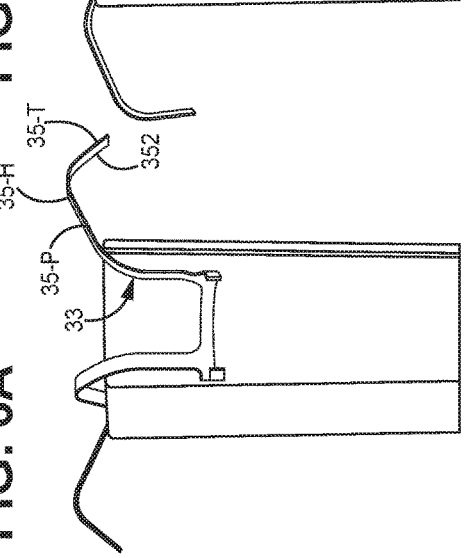

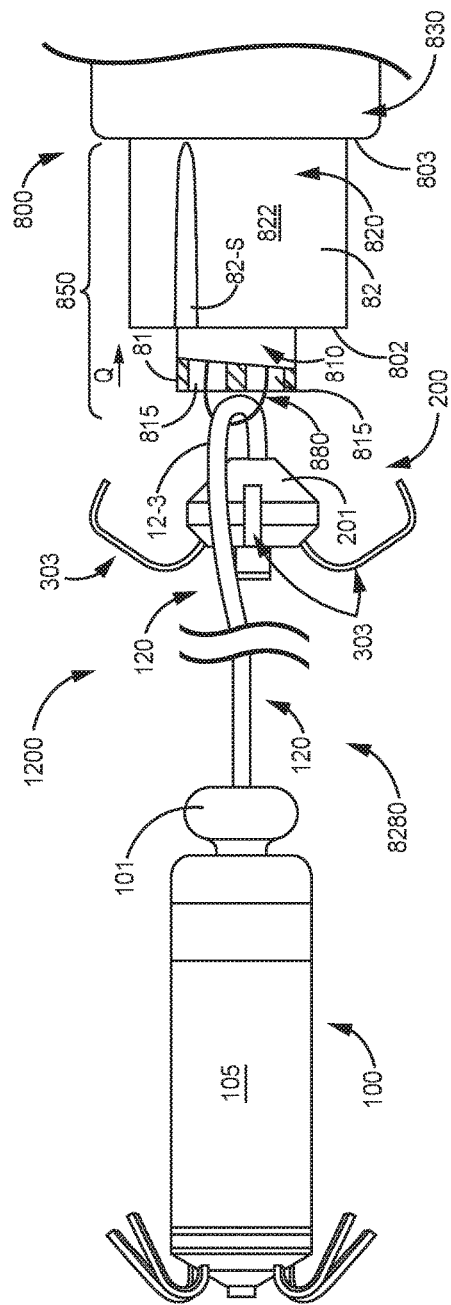
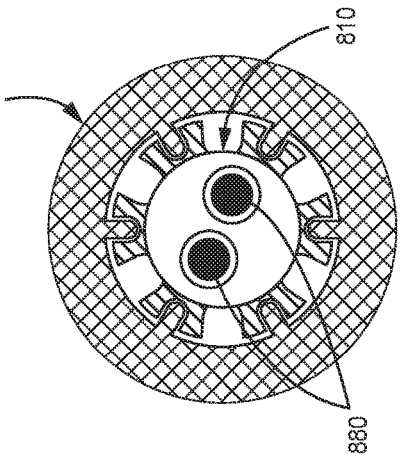
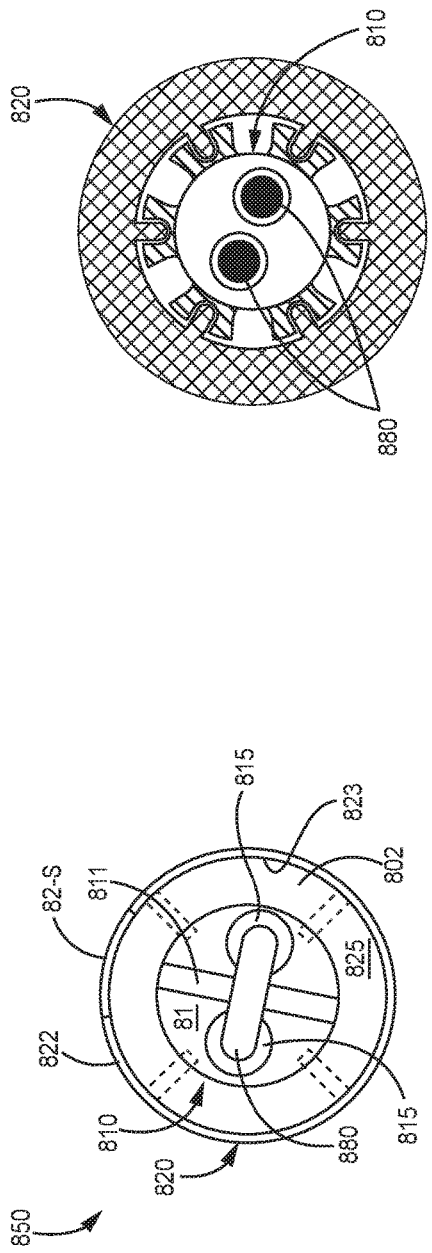
FIG. 8A
FIG. 8C
FIG. 8B

INTERVENTIONAL MEDICAL SYSTEMS

CROSS-REFERENCE TO RELATED APPLICATIONS

The instant application claims priority to U.S. Provisional Patent Application having the same title, the Ser. No. 62/281,312, which was filed on Jan. 21, 2016, and which is hereby incorporated by reference in its entirety. The instant application is also related to the U.S. patent application Ser. No. 15/410,161 and entitled, INTERVENTIONAL MEDICAL DEVICES, DEVICE SYSTEMS, AND FIXATION COMPONENTS THEREOF, which is filed concurrently herewith.

FIELD OF THE DISCLOSURE

The present disclosure pertains to interventional medical systems, and, more particularly, to relatively compact implantable medical devices and delivery tools thereof.

BACKGROUND

The traditional implantable cardiac pacemaker includes a pulse generator device to which one or more flexible elongate lead wires are coupled. The device is typically implanted in a subcutaneous pocket, remote from the heart, and each of the one or more lead wires extends therefrom to a corresponding electrode, coupled thereto and positioned at a pacing site, either endocardial or epicardial. Mechanical complications and/or MRI compatibility issues, which are sometimes associated with elongate lead wires and well known to those skilled in the art, have motivated the development of implantable cardiac pacing devices that are wholly contained within a relatively compact package, the entirety of which is configured for implant in close proximity to a pacing site. Such a relatively compact intra-cardiac device configured for dual chamber pacing may be implanted as shown in the schematic diagram of FIG. 1. FIG. 1 illustrates a dual chamber intra-cardiac pacing device including a first portion 10 implanted in a right ventricle RV of a heart, in proximity to an apex thereof, and a second portion 20 implanted in a right atrium RA of the heart, within an appendage 102 thereof. FIG. 1 further illustrates the device including a leadlet 12 that connects first portion 10 to second portion 20. There is a need for improved interventional medical systems facilitating the implant of relatively compact intra-cardiac dual chamber pacing devices like that illustrated in FIG. 1.

BRIEF SUMMARY

According to embodiments disclosed herein, an implantable medical device includes a ventricular portion, which has an electrode and a fixation mechanism, both mounted in proximity to a distal end of a hermetically sealed housing of the ventricular portion, an atrial portion, which has a core extending from a first end thereof to a second end thereof, along a longitudinal axis of the atrial portion, and a flexible leadlet that extends from a proximal end of the ventricular portion housing to the first end of the atrial portion core, the leadlet being coupled to an atrial electrode mounted in proximity to the second end of the core; wherein the atrial portion includes an open channel formed along the core thereof, the open channel extending between the first and second ends of the core and being sized to receive the leadlet therein, when the leadlet is folded over on itself.

According to some embodiments, a plurality of elastically deformable tines form a fixation mechanism of the atrial portion and are fixedly mounted to the core, being spaced apart from one another around a perimeter of the core. Each tine preferably includes: a proximal, spring portion being fixedly attached to the atrial portion core and having a spring-biased pre-formed curvature, the pre-formed curvature, in proximity to the core, extending in a first direction, generally parallel to the axis of the atrial portion, and then sweeping laterally, outward from the axis; and a distal portion including a proximal section, a hook section, and tip section terminated by a rounded free distal end, the proximal section extending from the proximal, spring portion and being pre-formed to extend in a second direction and along a relatively straight line to the hook section, the proximal section being oriented, by the spring-biased pre-formed curvature of the proximal, spring portion, so that the second direction is generally opposite the first direction, and the relatively straight line intersects the axis at an acute angle of between about 30 degrees and about 50 degrees, the hook section having a deformable pre-formed curvature that extends from the proximal section back toward the axis of the atrial portion, the tip section being pre-formed to extend along a relatively straight line from the hook section to the rounded free distal end, and the tip section being oriented, by the pre-formed curvature of the hook section, when undeformed, to extend toward the axis of the atrial portion, such that the tip section and the proximal section enclose an angle in a range from about 90 degrees to about 120 degrees; and wherein, when the atrial portion of the device is loaded within a tubular sidewall of a delivery tool, so that the rounded free distal end of each tine engages an inner surface of the sidewall, to hold the proximal, spring portion of each tine in a spring-loaded condition, each tip section of the distal portion extends away from the axis of the atrial portion at an acute angle in a range from about 45 degrees to about 75 degrees for deployment of the corresponding rounded free distal end out from the tool tubular sidewall; and upon deployment of the rounded free distal end of each tine, the tip section of each distal portion rotates away from the axis to approach an angle of 90 degrees, relative to the axis, in response to an initial release of the spring-loaded condition of the corresponding proximal, spring portion.

The device may be included in an interventional medical system along with a delivery tool that includes a tubular sidewall and a tether extending therein, the tubular sidewall defining a lumen and having a slot formed therein, wherein the slot extends proximally from an open end thereof, which is coincident with a distal opening of the lumen. The device is loaded in the delivery tool such that the second end of the atrial portion core faces the proximal end of the ventricular portion housing, such that the atrial portion thereof is contained within the lumen with a segment of the leadlet extending alongside the atrial portion, and with another segment of the flexible leadlet being folded over on itself proximal to the atrial portion, and such that the tether is engaged with the other segment of the leadlet at a fold therein. The slot of the tool is configured to allow passage of the flexible leadlet therethrough when the atrial portion is positioned in proximity to the distal opening of the lumen for deployment from the tool.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals denote like elements, and:

FIG. 6A is a schematic showing a spring loaded condition of the fixation component of the atrial portion of the device, according to some embodiments;

FIG. 6B is a schematic showing an initial release of the fixation component from the spring loading shown in FIG. 6A;

FIG. 6C is a schematic showing rotation for initial penetration of the fixation component after the initial release of FIG. 6B;

FIG. 6D is a schematic showing fixation component movement, subsequent to initial penetration;

FIG. 6E is a schematic showing fixation component movement, subsequent to penetration;

FIG. 6F is a schematic showing fixation component movement, subsequent to penetration;

FIG. 8A is a plan view, with a partial cut-away section, of a portion of an interventional medical system, according to some alternate embodiments;

FIG. 8B is an end view of an inner assembly of a delivery tool of the system of FIG. 8A, according to some embodiments;

FIG. 8C is an exemplary cross-section view through the inner assembly, according to some embodiments;

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives.

Figure 1:
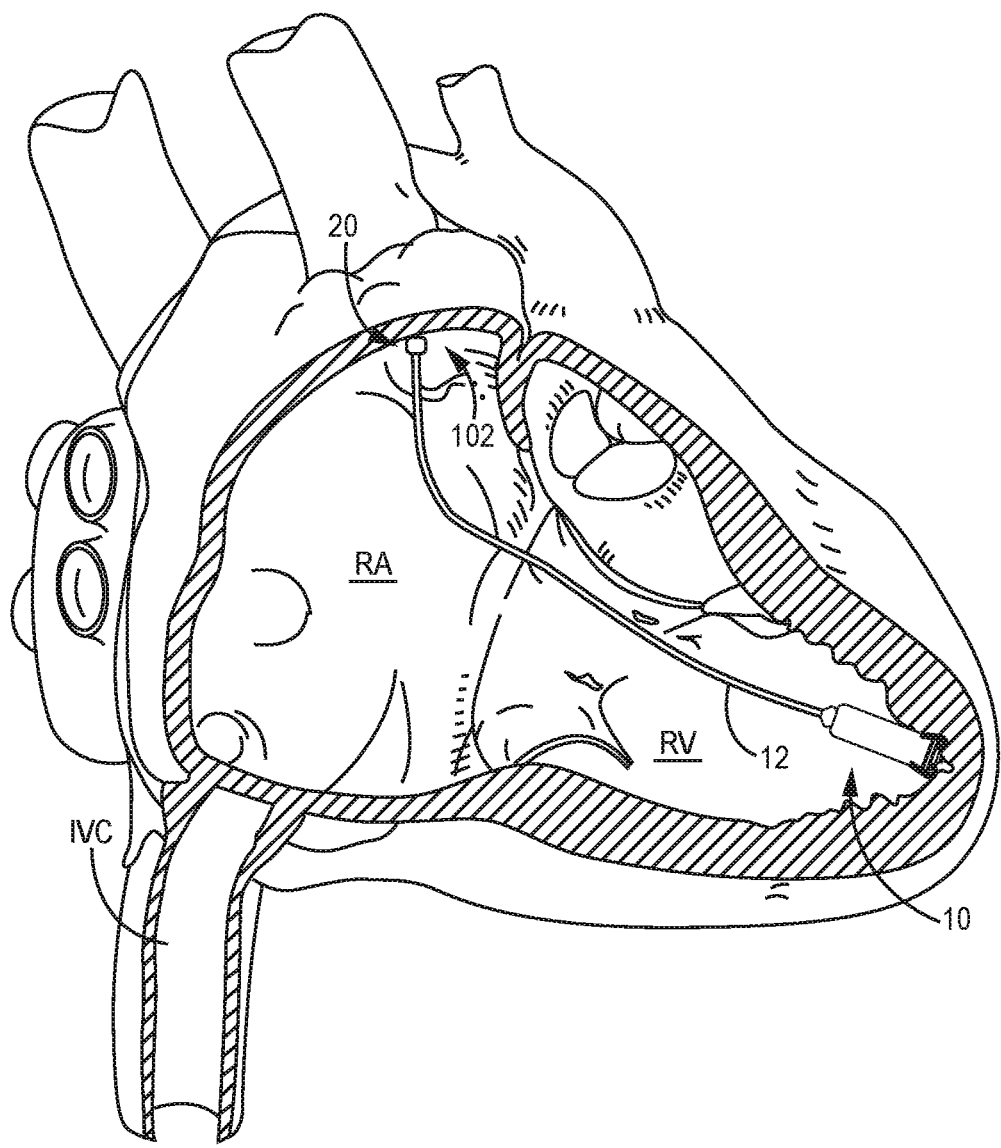
FIG. 1 is a schematic diagram showing an exemplary dual chamber intra-cardiac pacing device implanted in a right side of a heart.
Figure 2A:
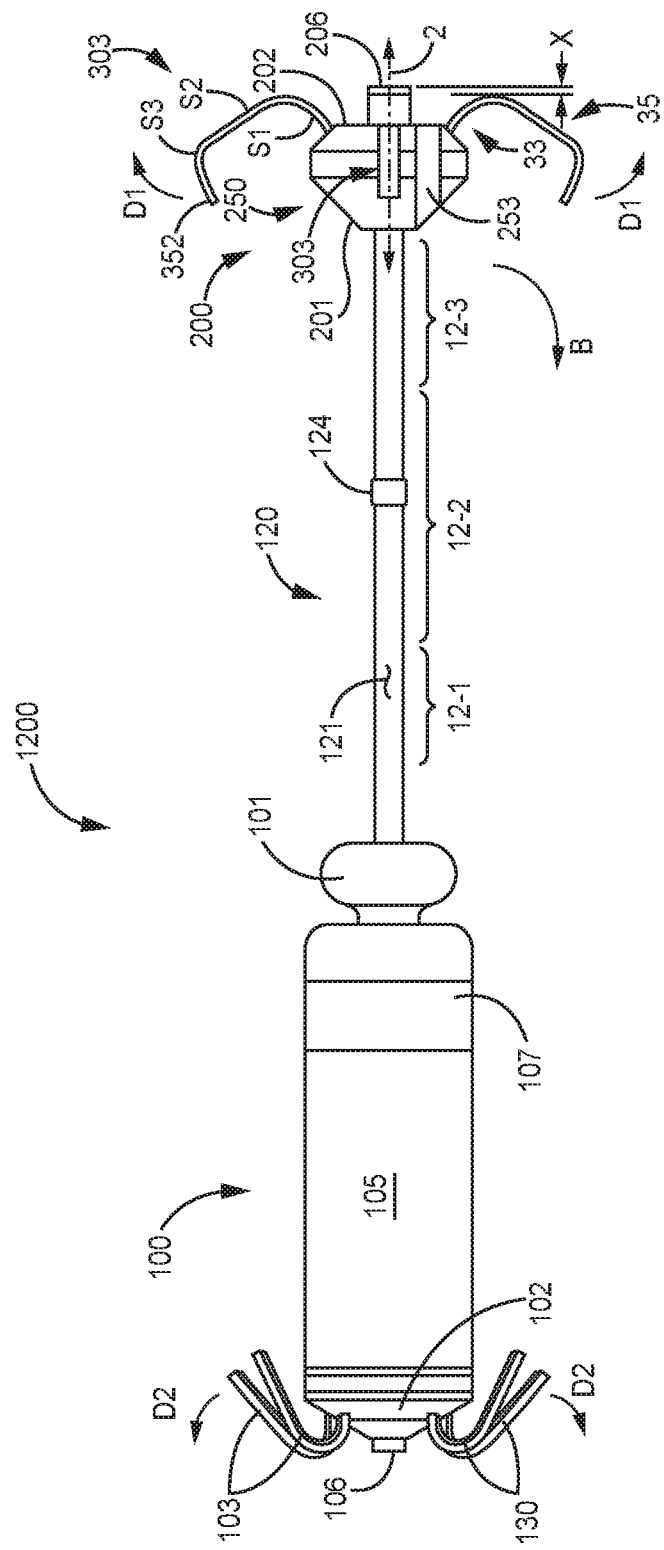
FIG. 2A is a plan view of a relatively compact dual chamber intra-cardiac pacing device, according to some embodiments.

FIG. 2A is a plan view of a relatively compact dual chamber intra-cardiac pacing device 1200, according to some embodiments. FIG. 2A illustrates device 1200 including a ventricular portion 100, an atrial portion 200, and a flexible leadlet 120 that connects ventricular portion 100 to atrial portion 200. Ventricular portion 100 is shown including a hermetically sealed housing 105, preferably formed from a biocompatible and biostable metal such as titanium, which contains a pulse generator (e.g., a power source and an electronic controller—not shown), a plurality of fixation tines 103, and an electrode 106, for example, being coupled to the pulse generator by a conductor of an hermetic feedthrough assembly (not shown) that is constructed according to methods known to those skilled in the art of implantable medical devices. Housing 105 may be overlaid with an insulative layer, for example, medical grade polyurethane, parylene, or silicone, and another electrode 107 may be formed by removing a portion of the insulative layer to expose the metallic surface of housing 105. According to the illustrated embodiment, electrode 106 may function for bipolar pacing and sensing, in conjunction with electrode 107, when elastically deformable fixation tines 103 hold electrode 106 in intimate tissue contact at a target implant site, for example, within right ventricle RV as illustrated schematically in FIG. 1. Exemplary embodiments of fixation tines 103 are described in commonly assigned U.S. Pat. No. 9,155,882, which is hereby incorporated by reference in its entirety.

With further reference to FIG. 2A, atrial portion 200 includes a core 250 that extends from a first end 201 thereof to a second end 202 thereof, along a longitudinal axis 2 of atrial portion 200, and to which another electrode 206 is mounted, in proximity to second end 202. Leadlet 120 is shown extending from a proximal end 101 of device ventricular portion 100 to first end 201 of core 250. According to the illustrated embodiment, a conductor 122 (FIG. 4B) of leadlet 120, which extends through another hermetic feedthrough assembly (not shown) of ventricular portion 100, and within an insulative tubular member 121 of leadlet 120, electrically couples the aforementioned pulse generator (contained within housing 105) to electrode 206. Conductor 122 may be formed by one or more wires, for example, MP35N alloy known to those skilled in the art, in a coiled or cabled configuration; and insulative tubular member 121 may be any suitable medical grade polymer, for example, polyurethane, silicone rubber, or a blend thereof. Core 250 may be formed from any suitable medical grade polymer, such as, polyurethane, silicone, polyethylene, or polyether ether ketone (PEEK), for example, being insert molded around a shank (not shown) of electrode 206, to which conductor 122 is coupled. According to an exemplary embodiment, a length of flexible leadlet 120, from proximal end 101 of ventricular portion housing 105 to first end 201 of atrial portion core 250 is in a range from about 15 cm to about 20 cm. It should be noted that, according to some alternate embodiments, atrial portion 200 includes another electrode mounted to core 250 and spaced apart from electrode 206, toward first end 201, to provide bipolar pacing and sensing in right atrium RA. In this case, leadlet 120 includes a pair of conductors isolated from one another, to electrically couple each atrial electrode to the pulse generator.

FIG. 2A further illustrates atrial portion 200 including a plurality of elastically deformable fixation tines 303 spaced apart around a perimeter of core 250 and being fixedly mounted thereto, for example, via a base 301 to which each tine 303 is joined, as described below in conjunction with FIGS. 3A-B. According to the illustrated embodiment, elastically deformable fixation tines 303 hold electrode 206 of atrial portion 200 in intimate tissue contact at a target implant site within right atrium RA, for example, as illustrated schematically in FIG. 2B. In FIG. 2A, one of tines 303 is shown divided into first, second, and third segments S1, S2, S3, each of which is pre-formed into, and elastically deformable from, the illustrated shape thereof. According to the illustrated embodiment, each first segment S1 is fixedly attached to core 250, and extends around a pre-formed curvature to the corresponding second segment S2, which extends proximally along a relatively straight line to the corresponding third segment S3. FIG. 2A illustrates third segment S3 extending around a pre-formed curvature to a free distal end 352 of tine 303.

Figure 2B:
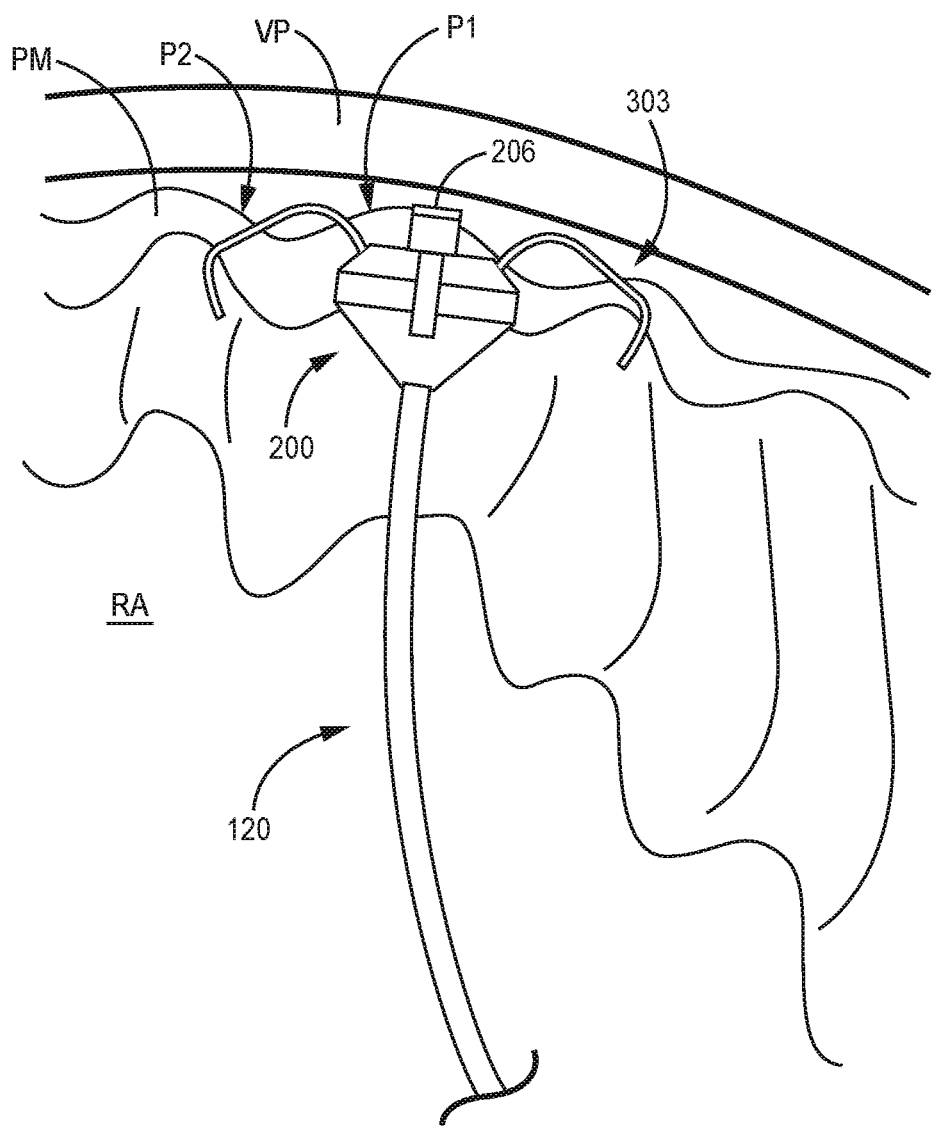
FIG. 2B is a schematic section showing an atrial portion of the device of FIG. 2A implanted, according to some embodiments and methods.

FIG. 2B is a schematic section showing atrial portion 200 of device 1200 implanted in right atrium RA, according to some embodiments and methods. With reference to FIG. 2B, a portion the right atrial wall, for example, in appendage 102 (FIG. 1), is shown having a laminate structure that includes an inner layer of pectinate muscle PM and an outer layer of visceral pericardium VP, which forms the epicardial surface. FIG. 2B illustrates atrial portion 200 secured at the implant site by fixation tines 303 penetrating through the layer of pectinate muscle PM without perforating through visceral pericardium VP, which could result in pericardial effusion. Tines 303, according to embodiments disclosed herein, are configured for spring-loaded release when atrial portion 200 of device 1200 is deployed out through a distal opening of a delivery tool, for example, a distal opening 403 of a lumen 435 of a delivery tool 400 in an interventional medical system 1240 (FIGS. 4A-B), or a distal opening 802 of a lumen 825 of a delivery tool 800 of a system 8280 (FIGS. 8A-E). In either case, upon release of the spring loading, the free distal end 352 penetrates pectinate muscle PM without perforating visceral pericardium VP. It should be noted that alternate suitable implant sites for embodiments of fixation member tines described herein can be along any endocardial surface defined by pectinate muscle PM. The spring-loaded release and exemplary methods for deploying device 1200 are described below in conjunction with FIGS. 4A-B, 5A-B, 6A-F, 7A-B, 8A-E, and 9A-C. However, implantable medical devices having alternative tine configurations, for example, those more suitable for fixation to endocardial surfaces where pectinate muscle PM is not present, can be employed by the systems and methods described below, and such systems and methods are not outside the scope of the present invention.

Figure 3A:
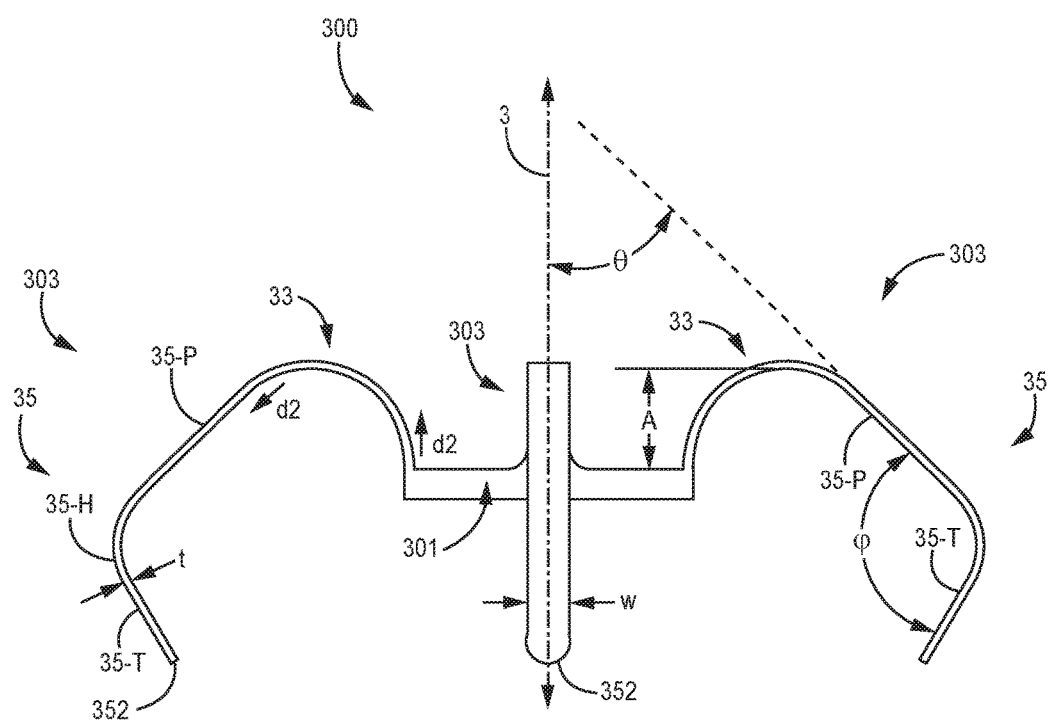
FIG. 3A is an elevation view of an exemplary fixation component which may be employed by the atrial portion of the device, according to some embodiments.
Figure 3B:
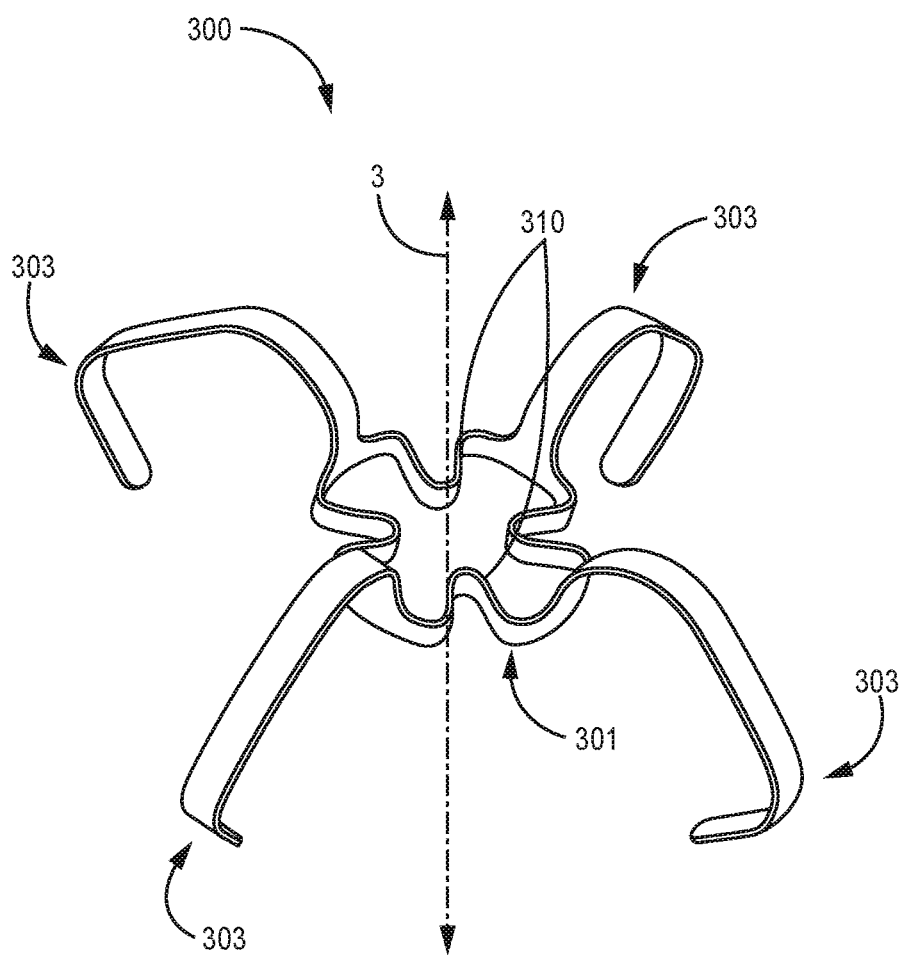
FIG. 3B is a perspective view of the component of FIG. 3A, according to some embodiments.

FIGS. 3A-B are elevation and perspective views of a fixation component 300 that forms the fixation mechanism for atrial portion 200 of device 1200, according to some embodiments. FIGS. 3A-B illustrate the aforementioned base 301 from which a plurality of tines 303 extend, being spaced apart from one another around a perimeter of base 301. Tines 303 are shown in a relaxed, or pre-formed spring-biased condition. In FIG. 3A, a longitudinal axis 3 of component 300 is shown being defined by base 301 such that, when base 301 is mounted around atrial portion core 250, and a perimeter of component 300 extends around electrode 206, axis 3 is generally aligned along longitudinal axis 2 of atrial portion 200 (FIG. 2A). With reference to FIG. 3B, base 301 is shown including an inward bending segment 310 directed toward axis 3 between each adjacent pair of tines 303. With reference back to FIG. 2A, when component 300 is mounted on core 250 of device atrial portion 200, each of inward bending segments 310 may provide clearance for a groove, or open channel 253 of atrial portion 200, which can be a molded feature of core 250. Core 250 may be inserted molded around component 300, or component 300 may be snap fit, staked or bonded to a separately-molded core 250, according to methods known in the art. (However, in some alternate embodiments, tines 303 may be individually mounted to core 250 without being integrated together by any base.) FIG. 2A illustrates channel 253 extending between first and second ends 201, 202 of core 250. According to the illustrated embodiment, channel 253 is sized to receive leadlet 120 therein, for example, to provide clearance for leadlet 120 to extend alongside core 250 within delivery tool 400, as will be described below in conjunction with FIGS. 4A-B. Although only one channel 253 is shown in FIG. 2A, some embodiments of core 250 include a plurality of channels 253, for example, one between each adjacent pairs of tines 303, as shown in FIG. 4B.

Tines 303 are preferably formed from a super-elastic material, for example, a Nickel-Titanium alloy (Nitinol). Fixation component 300 may be cut from a medical grade Nitinol tubing that conforms to the chemical, physical, mechanical, and metallurgical requirements of the ASTM F2063 standard, and has a wall thickness of about 0.005 inch. In this case, tines 303 are integrally formed with base 301 and each tine 303 may have a constant thickness t of 0.005 inch±0.001 inch. After cutting the tubing, tines 303 and base 301 are formed into the configuration shown in FIGS. 3A-B by holding each in the illustrated shape, while heat treating according to methods known to those skilled in the art.

FIG. 3A illustrates each tine 303 including a proximal, spring portion 33, which corresponds to first segment S1 of FIG. 2A, and a distal portion 35, which corresponds to second and third segments S2, S3 of FIG. 2A, and which is terminated by free distal end 352. Free distal end 352 is preferably rounded, as shown in FIG. 3A. FIG. 3A further illustrates distal portion 35 including a proximal section 35-P, a hook section 35-H, and a tip section 35-T. The shaped configuration and width of each tine 303, along with the super-elastic stiffness properties of Nitinol, provide a sufficient spring force and structural stiffness for tines 303 to engage tissue for the fixation of device atrial portion 200 at an implant site when deployed by delivery tool 400 or delivery tool 800, as described in greater detail below. With reference to FIG. 3A, each tine 303 has a width w which is preferably no less than about 0.02 inch, for example, being in a range from about 0.025 inch to about 0.032 inch. Such a width provides the aforementioned structural stiffness, as well as a radiopaque density that facilitates fluoroscopic visualization during and after the implant procedure.

With further reference to FIG. 3A, according to the illustrated embodiment, each proximal, spring portion 33 is fixedly attached to base 301 and has a spring-biased pre-formed curvature, which, in proximity to the base, extends in a first direction d1, generally parallel to axis 3, and then sweeps laterally, outward from axis 3 to distal portion proximal section 35-P. Distal portion proximal section 35-P, according to the illustrated embodiment, is pre-formed to extend in a second direction d2 and along a relatively straight line (dashed line), being oriented, by the spring-biased pre-formed curvature of proximal, spring portion 33, so that second direction d2 is generally opposite first direction d1, and the relatively straight line intersects axis 3 at an acute angle θ. According to some embodiments, angle θ is between about 30 degrees and about 50 degrees. In an exemplary embodiment of component 300, to be employed by an exemplary embodiment of device 1200 in which atrial portion core 250 has an outer diameter of about 0.26 inch (20 French), the spring-biased pre-formed curvature of each proximal, spring portion 33 is defined by a single radius of 0.067 inch±0.010 inch; a distance A between base 301 and each intersection of proximal, spring portion 33 and distal portion proximal segment 35-P is 0.092 inch±0.005 inch; a length of each distal portion proximal segment 35-P is 0.100 inch±0.005 inch; and angle θ is about 45 degrees.

With further reference to FIG. 3A, each distal portion hook section 35-H has a deformable pre-formed curvature that extends from proximal, spring portion 33 back toward axis 3. FIG. 3A further illustrates tip section 35-T of distal portion 35 extending from hook section 35-H along a relatively straight line to rounded free distal end 352. Tip section 35-T is shown oriented by the pre-formed curvature of hook section 35-H, when un-deformed, to extend toward axis 3, such that tip section 35-T and proximal section 35-P are shown enclosing an angle φ, which, according to the illustrated embodiment, is no less than about 90 degrees, but can be up to about 120 degrees. In the aforementioned exemplary embodiment of component 300, the deformable pre-formed curvature of each hook section 35-H, when un-deformed, is defined by a single radius of about 0.05 inch; and a length of each tip section 35-T is 0.064 inch±0.005 inch.

Figure 3C:
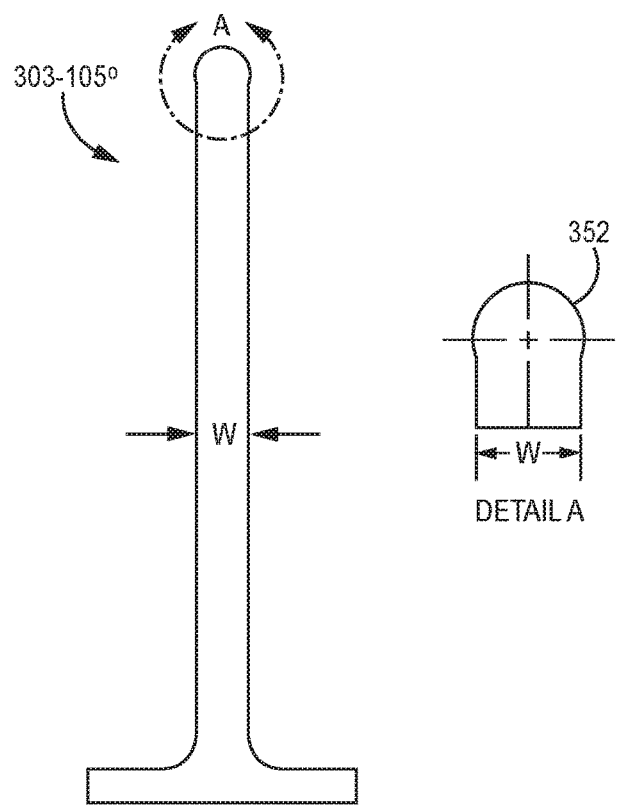
FIG. 3C is a plan view of a portion of the component of FIGS. 3A-B, prior to forming, according to some embodiments.
Figure 3D:
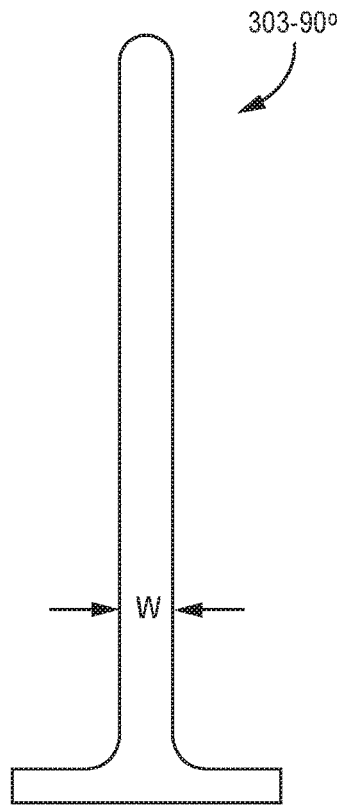
FIG. 3D is a plan view of a portion of the component of FIGS. 3A-B, prior to forming, according to some alternate embodiments.

FIGS. 3C-D are plan views of alternate tine embodiments prior to being formed into the configuration of FIG. 3A, wherein tine 303-105° of FIG. 3C is suitable for an exemplary component 300 in which angle φ is about 105 degrees, and wherein tine 303-90° of FIG. 3D is suitable for an exemplary component 300 in which angle φ is about 90 degrees. With further reference to FIGS. 3C-D, an exemplary width w of each tine 303 is 0.028 inch±0.001 inch, and, in the tine embodiment of FIG. 3C, rounded free distal end 352 of tine 303-105° has an enlarged width defined by a diameter of 0.030 inch±0.001 inch.

Figure 4A:
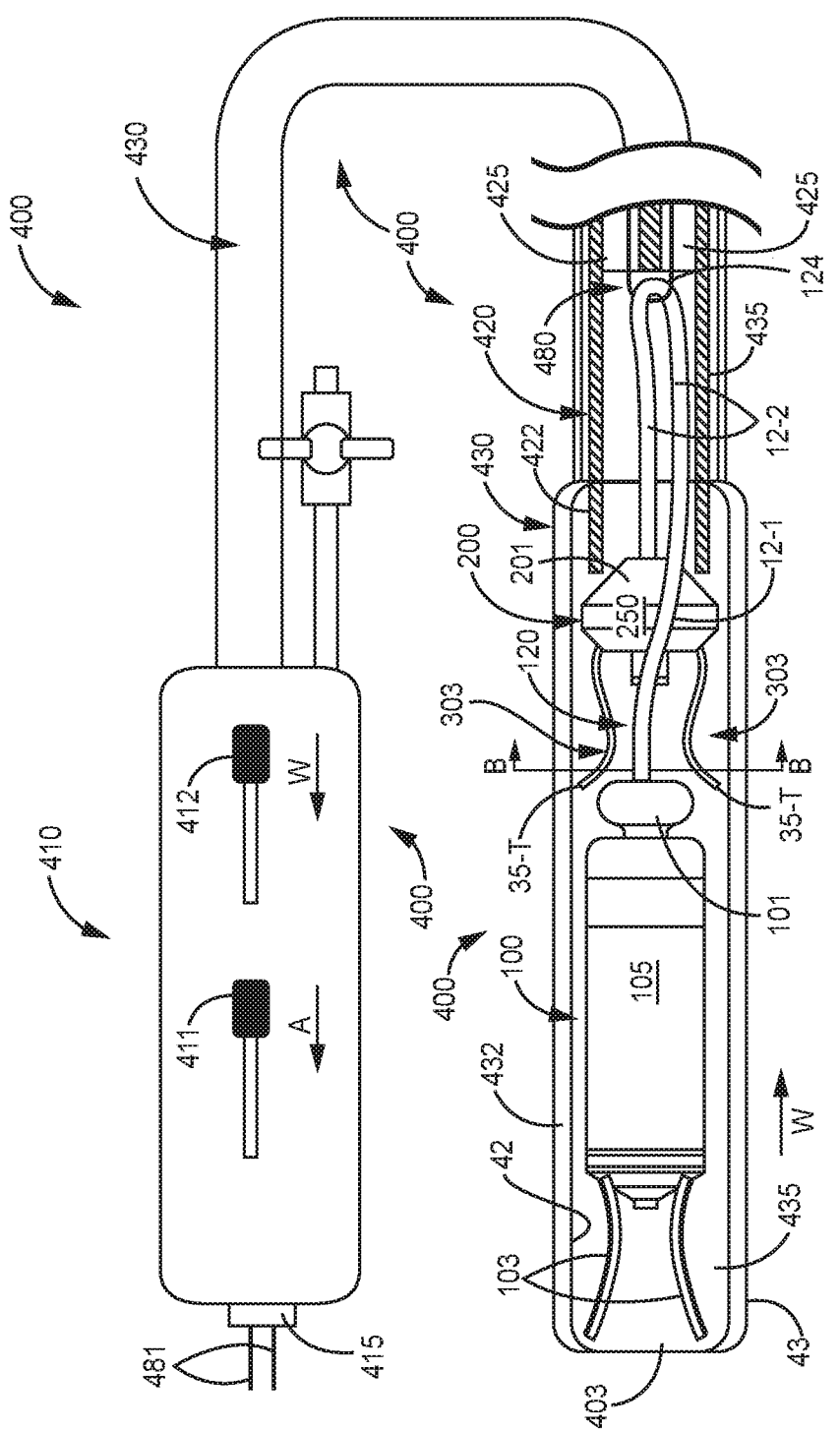
FIG. 4A is a plan view, with a partial cut-away section, of an interventional medical system, according to some embodiments.
Figure 4B:
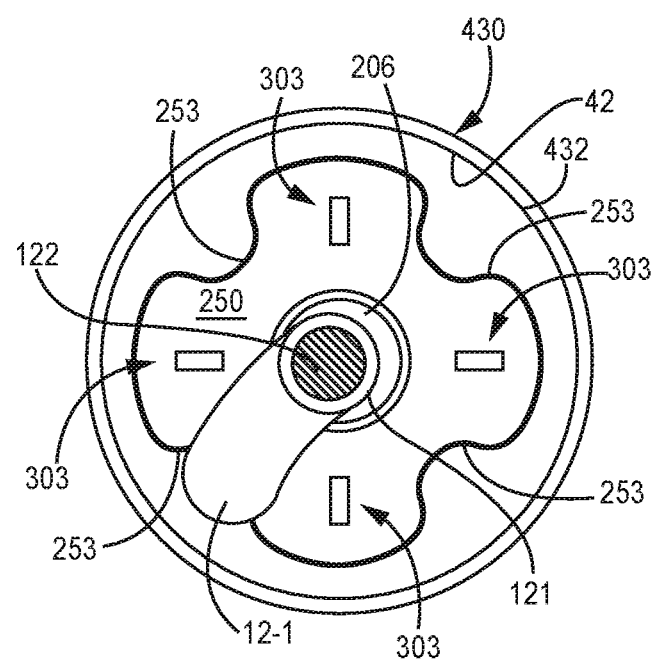
FIG. 4B is a cross-section view through section line B-B of FIG. 4A, according to some embodiments.

FIG. 4A is a plan view, with a partial cut-away section, of interventional medical system 1240, according to some embodiments, which includes device 1200 (FIG. 2A) and delivery tool, wherein device 1200 is shown loaded in delivery tool 400 for deployment; and FIG. 4B is a cross-section view through section line B-B of FIG. 4A, according to some embodiments. FIG. 4A illustrates tool 400 including a handle 410, an elongate outer member 430, and an elongate inner member 420, which extends within lumen 435 of outer member 430, and around which outer member 430 is slideably engaged, for example, via a control member 412 of handle 410, as described below. FIG. 4A further illustrates inner member 420 including a distal end 422, which is configured to engage device atrial portion 200 by abutting first end 201 of core 250. An entirety of device 1200 is shown loaded within a tubular sidewall 432 of outer member 430 that defines a distal portion of outer member lumen 435. With reference back to FIG. 2A, prior to loading device 1200 into delivery tool 400, atrial portion 200 is reoriented relative to ventricular portion 100 by bending leadlet 120, per arrow B, so that a first segment 12-1 of leadlet 120 extends within open channel 253 of core 250, so that a second segment 12-2, folded over on itself, extends within distal end 422 of inner member 420, and so that tines 303 are adjacent ventricular portion proximal end 101. To load device 1200 into tool 400, the operator may employ a tether 480 of tool 400 (seen in FIG. 4A) by engaging tether 480 around leadlet 120 at a zone 124 (FIG. 2A) that coincides with the aforementioned fold per arrow B. According to the illustrated embodiment, opposing lengths of tether 480 extend within lumens 425 of inner member 420 so that tether 480 loops around leadlet 120 for engagement therewith, and proximal ends 481 of the tether lengths protrude from a proximal port opening 415 of delivery tool 400, where an operator may grasp them. The operator may pull ends 481 of tether 480, to draw folded segment 12-2 of leadlet 120 in through a distal opening 403 of lumen 435, followed by atrial portion 200, with core first end 201 leading, and then followed by ventricular portion 100. FIG. 4A illustrates tether 480 looped around zone 124 such that folded second segment 12-2 of leadlet 120 extends within distal end 422 of inner member 420, when device 1200 is loaded in delivery tool 400, and, with reference to FIG. 4B, first segment 12-1 of leadlet 120 can be seen extending in one of a plurality of channels 253 of core 250, according to some embodiments. It should be noted that a snare-type tool, such as is known to those skilled in the art, may be employed in lieu of tether 480, such that the term "tether" may broadly refer to such a snare. According to the illustrated embodiment, an inner surface 42 of tubular sidewall 432 first engages fixation tines 303 of atrial portion 200, and then ventricular portion tines 103, as device 1200 is pulled into lumen 435, to deform each set of tines 103, 303, per arrows D1 and D2 (FIG. 2A), respectively, and to hold tines 103, 303 of the loaded device 1200 in a spring-loaded condition, for example, as shown in FIG. 4A. According to the above-described exemplary embodiments of fixation tines 303, when atrial portion core 250 and ventricular portion housing 105 are each sized to an outer diameter of about 0.26 inch (20 French), a diameter of lumen 435, defined by inner surface 42, is about 0.28 inch (21 French). In alternate embodiments, described below, starting with FIG. 8A, an implantable device includes an atrial portion that is down-sized relative to the ventricular portion. With further reference to FIG. 4A, a proximal end of outer member 430 is coupled to control member 412 of handle 410 such that an entirety of outer member 430 is movable with respect to inner member 420, via control member 412; thus, an operator may retract outer member 430, per arrow W, relative to device 1200 and inner member 420, to deploy device 1200 out through distal opening 403. According to the illustrated embodiment, and with reference back to FIG. 1, the operator first deploys ventricular portion 100 of device 1200 at an implant site in right ventricle RV of the patient, and then deploys atrial portion 200 at an implant site in right atrium RA of the patient.

Figure 5A:
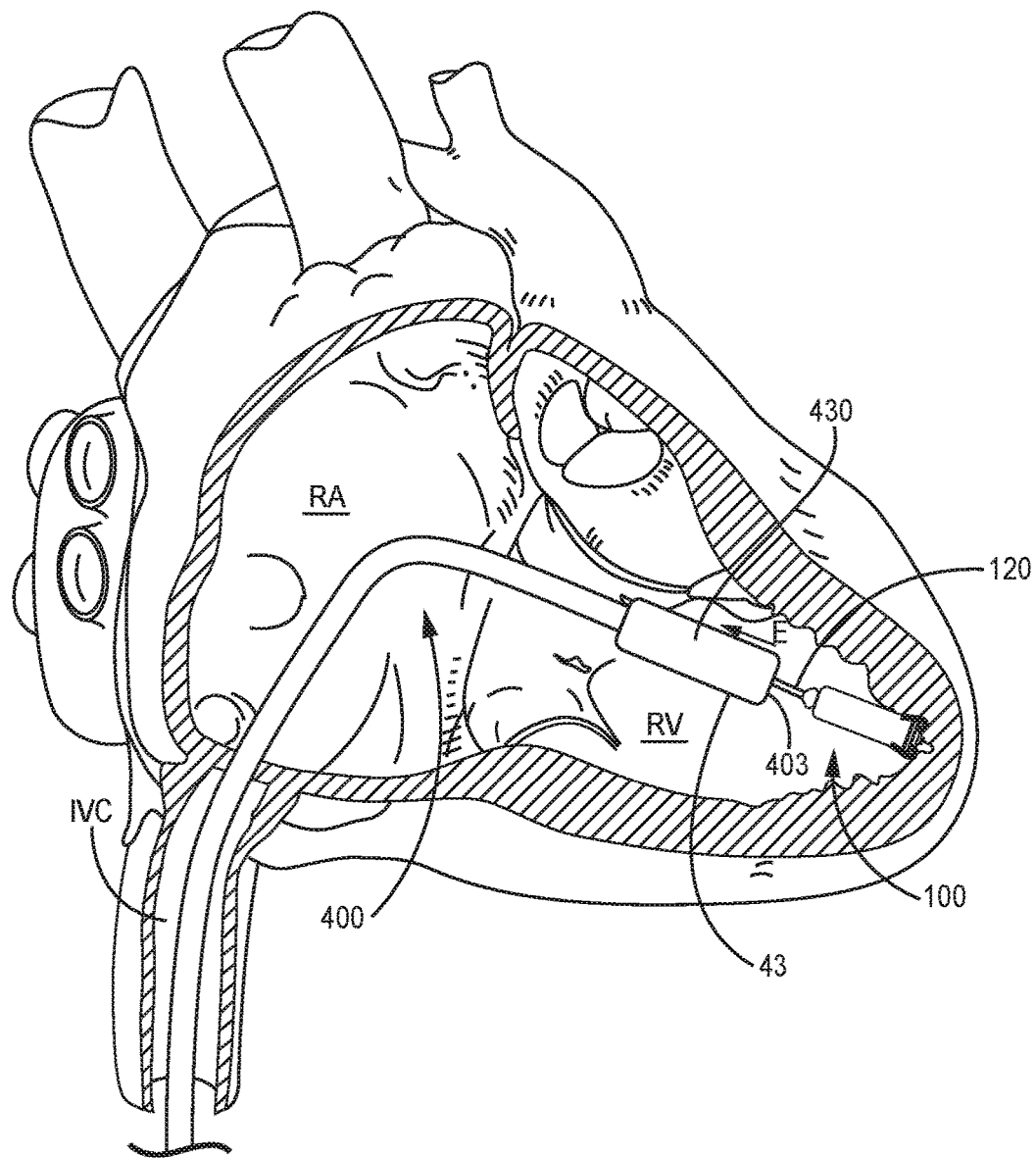
FIG. 5A is a schematic diagram of the system of FIG. 4A advanced into a right ventricle for deployment of a ventricular portion of the device of FIG. 2A.

FIG. 5A is a schematic diagram of system 1240 within right ventricle RV, after the operator has deployed ventricular portion 100. According to some methods, the operator deploys ventricular portion 100 by advancing system 1240 through a venous system of the patient, for example, from a femoral venous access site and up through an inferior vena cava IVC of the patient into right atrium RV and across the tricuspid valve into right ventricle RV, until a distal end 43 of delivery tool 400 abuts the target implant site. With distal end 43 abutting the implant site, the operator applies a push force through tool 400 while retracting outer member 430, as described above, to release fixation tines 103 of ventricular portion 100 out through distal opening 403 for engagement with tissue at the implant site. With reference back to FIG. 4A, the abutment of inner member 420 against first end 201 of core 250 of device atrial portion 200, and the abutment of tine tip sections 35-T of atrial portion 200 against proximal end 101 of device ventricular portion 100 together apply pressure to stabilize ventricular portion 100 as the operator withdraws outer member 430. With reference to FIG. 5A, once fixation tines 103 of ventricular portion 100 are completely released from the spring-loaded condition, for full engagement with tissue at the implant site, the operator withdraws, per arrow E, delivery catheter 400, with atrial portion 200 still contained therein, back into right atrium RA, while first segment 12-1 and second segment 12-2 of leadlet 120 slide through channel 253 of atrial portion core 250 and out through distal opening 403 of outer member 430.

Figure 5B:
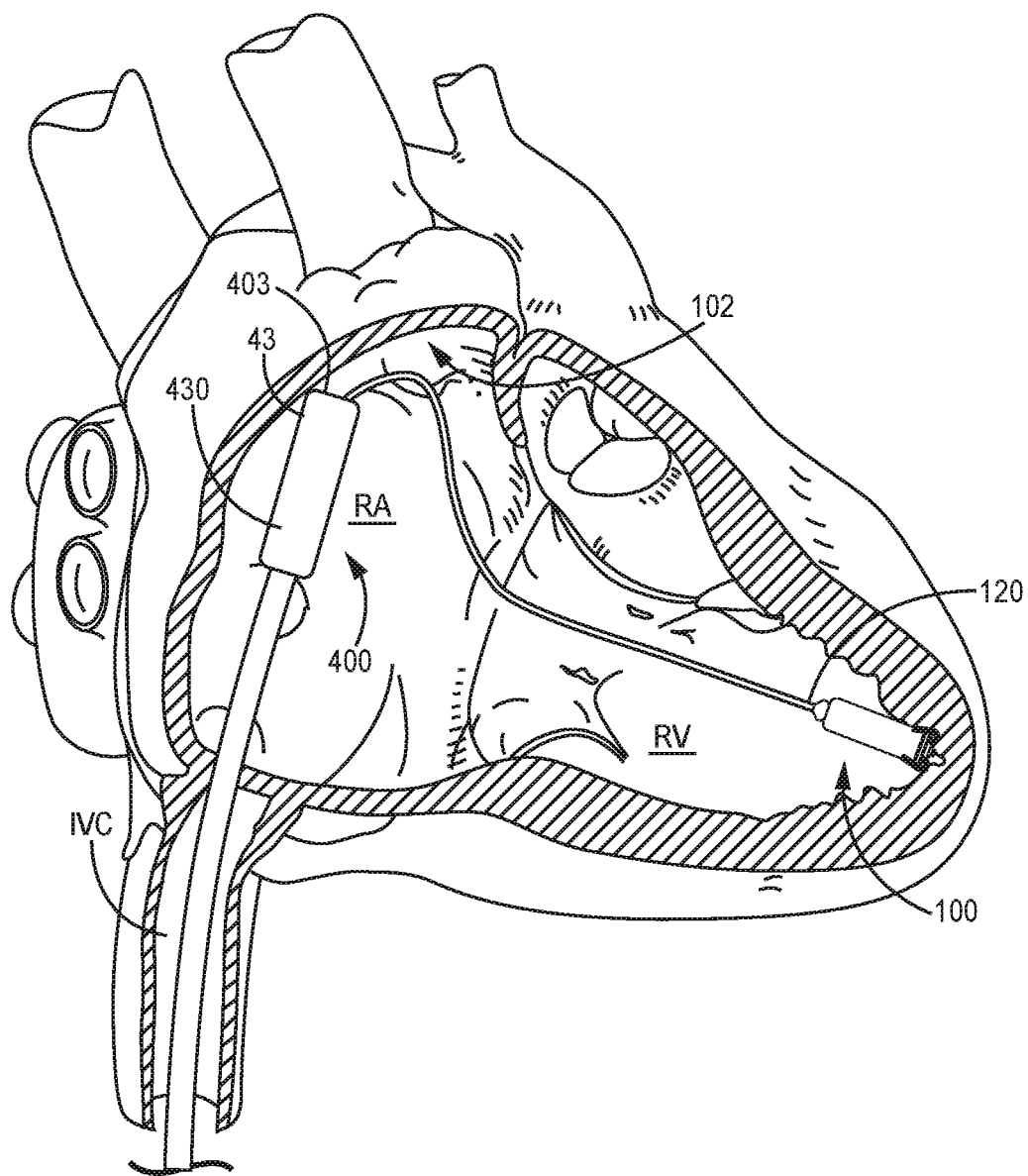
FIG. 5B is a schematic diagram of a delivery tool of the system positioned in a right atrium for deployment of the atrial portion of the device.
Figure 5C:
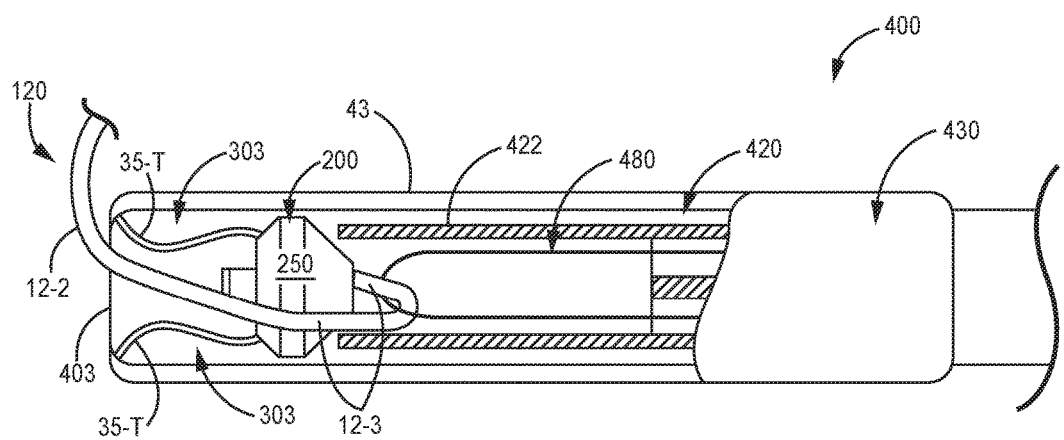
FIG. 5C is a cross-section view through a distal end of a delivery tool of the system, according to some embodiments.

FIG. 5B is a schematic diagram of delivery tool 400 positioned in right atrium RA for deployment of device atrial portion 200. FIG. 5B illustrates distal opening 403 of outer member 430 directed into atrial appendage 102 where the operator will abut distal end 43 against pectinate muscle PM (FIG. 2B) and apply a push force through delivery tool 400 prior to retracting outer member 430, relative to inner member 420 and atrial portion 200, to release the spring loading of fixation tines 303 for engagement with pectinate muscle PM at the implant site, as shown in FIG. 2B. FIG. 5C is a cross-section view through distal end 43 of delivery tool 400 showing atrial portion 200 positioned for deployment. With reference to FIG. 5C, it may be appreciated that tether 480 was free to move distally, as the operator retracted delivery tool 400 from right ventricle RV into right atrium RA, and leadlet first and second segments 12-1, 12-2 slid out through distal opening 403. FIG. 5C illustrates a third segment 12-3 of leadlet extending within channel 253 of core 250, and distal portion tip section 35-T of spring-loaded tines 303 located in close proximity to distal opening 403. (Leadlet third segment 12-3 is also shown in FIG. 2A, for reference.) The spring loaded condition of tines 303 is described in greater detail below, in conjunction with FIG. 6A.

Delivery tool 400 may include articulating features to facilitate the above-described navigation. For example, inner member 420 of delivery tool 400 may include a pull wire assembly (not shown) integrated therein. With reference back to FIG. 4A, the pull wire assembly may be coupled to another control member 411 of handle 410 that, when moved per arrow A, causes inner member 420 and outer member 430 to bend along distal portions thereof. A length of outer member 430, between handle 410 and distal opening 403, when outer member 430 is in the position shown in FIG. 4A, may be about 110 cm, for example, to reach into the right ventricle RV from the femoral access site. Suitable construction detail for a delivery tool like tool 400 is described in co-pending and commonly assigned U.S. Patent Application 2015/0094668, Ser. No. 14/039,937; (filed on Sep. 27, 2013), the description of which is hereby incorporated by reference. However, it should be noted that, according to some alternative embodiments and methods, delivery tool 400 may be configured so that an operator can move inner member 420 relative to outer member 430 to deploy one or both of ventricular and atrial portions 100, 200 of device 1200 out through distal opening 403, and, in these embodiments, inner member 420 and/or outer member 430 may include a pull wire assembly to facilitate navigation.

FIGS. 6A-F are schematics outlining a sequence of events corresponding to the release of the spring loading for above-described embodiments of fixation tines 303 for device atrial portion 200. (Although the schematics show tines 303 integrally formed with base 301, as in above-described embodiments of component 300, it should be understood that the sequence of events in FIGS. 6A-F may also apply to alternate embodiments in which tines 303 are not integrally formed with base 301.) FIG. 6A illustrates a maximum deformation of tines 303 when held in the spring-loaded condition by the engagement of rounded free distal end 352 with inner surface 42 of outer member tubular sidewall 432, wherein proximal, spring portion 33 becomes relatively straightened, and a location of the maximum principle strain along each tine 303 is in relatively close proximity to base 301 (designated by dashed-line circle). With reference back to FIG. 3A, the aforementioned exemplary length of distal portion tip section 35-T and the aforementioned associated angle φ (no less than 90 degrees) help to keep the deformed tines 303 from touching one another within lumen 435 and to prevent free distal ends 352 from being pulled proximally, per arrow P, when outer member 430 is retracted to release the spring loading of tines 303. FIG. 6A further illustrates tip section 35-T extending away from axis 3 at an acute angle δ, which is preferably in a range from about 45 degrees to about 75 degrees for an initial release of the spring loading of each tine 303, upon retraction of outer member 430, as depicted in FIG. 6B. With reference to FIG. 6C, once free distal end 352 is released from engagement with inner surface 42 for deployment into tissue at the implant site, the spring force of proximal, spring portion 33 and the pre-formed curvature of distal portion hook section 35-T cause distal portion tip section 35-T to immediately rotate away from axis 3 to an angle π, which approaches 90 degrees, so that tip section 35-T is oriented approximately normal to axis 3 for initial penetration of pectinate muscle PM. Thus each tine free distal end 352 is deployed in a direction toward pectinate muscle PM that ultimately prevents tines 303 from perforating the underlying visceral pericardium VP (reference FIG. 2B). FIGS. 6D-F illustrates the subsequent movement of tines 303, being driven by the release of proximal, spring portion 33 from the spring loading. According to the illustrated embodiment, this release of proximal, spring portion 33 causes free distal end 352, after penetrating through pectinate muscle PM in a first direction, at a first location P1, to penetrate back through in an opposite direction, at a second location P2, so that device 20 may be securely fixed at the implant site, as illustrated in FIG. 2B.

The configuration of tine distal portion 35, for example, embodied by the aforementioned exemplary lengths of proximal section 35-P and tip section 35-T, and the preformed curvature of hook section 35-H, provide a structural stiffness and reach to each tine 303 that is sufficient for deformation and subsequent penetration of free distal end 352 through pectinate muscle PM, as shown in FIG. 2B, but is not sufficient for penetration through visceral pericardium VP. Even if the operator ends up advancing the system into appendage 102 so that distal opening 403 of tool 400 abuts visceral pericardium VP, between folds of pectinate muscle PM, free distal end 352, according to this configuration of tines 303, is not backed-up by sufficient stiffness to penetrate through visceral pericardium VP, so tip section 35-T of tine distal portion 35 is redirected, laterally, toward pectinate muscle PM.

It should be noted that an operator may employ fixation component 300 to secure atrial portion 200 in atrial appendage 102 in an alternative fashion, wherein tines 303 are fully released from the spring-loaded condition without engaging any tissue (FIG. 6F), and then atrial portion 200 is advanced to the implant site so that tines 303 wedge between opposing surfaces of pectinate muscle PM within atrial appendage 102.

With reference back to FIGS. 2A-B, according to some embodiments, for example, in order to assure intimate contact of electrode 206 with tissue, when fixation component 300 secures atrial portion 200 at a target implant site, electrode 206 is spaced distally apart from second end 202 of atrial portion core 250 by a distance along longitudinal axis 2. Electrode 206 may be approximately flush with an intersection between proximal, spring portion 33 and distal portion 35, or spaced distally apart from the intersection by a distance X that may be up to about 2 mm, as depicted in FIG. 2A.

Figure 7A:
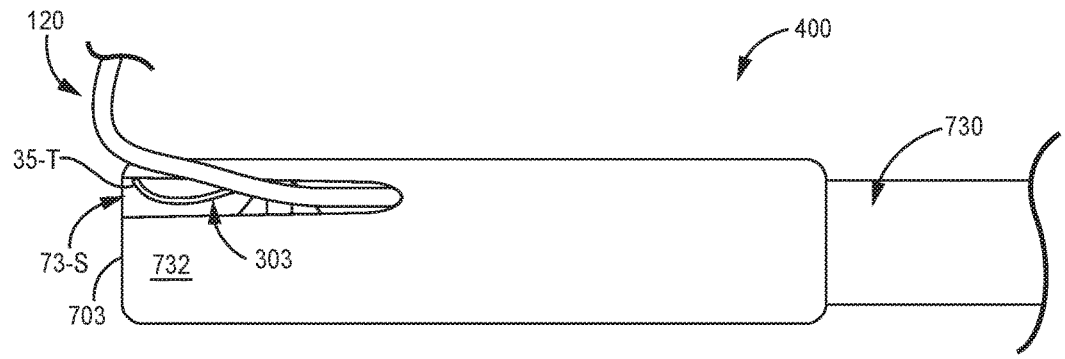
FIG. 7A is a plan view of a distal portion of an alternate embodiment of a portion of the system shown in FIG. 4A
Figure 7B:
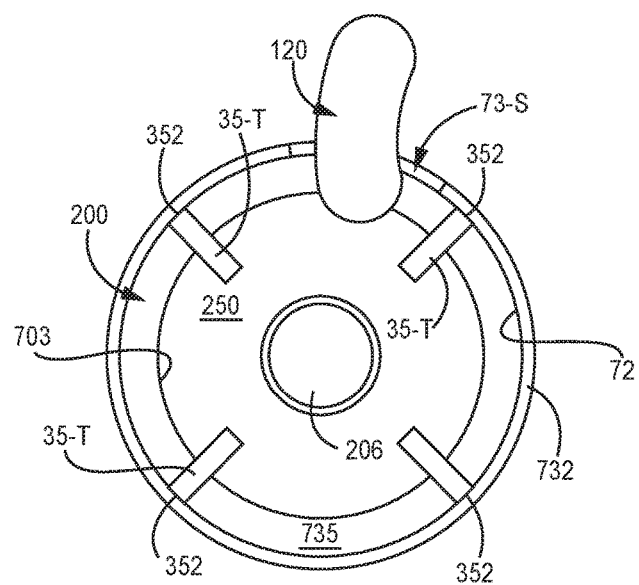
FIG. 7B is an end view of the distal portion of FIG. 7A.

With reference back to FIG. 5C, the position of leadlet 120, in proximity to distal opening 403 of delivery tool 400, may interfere with tines 303, when tip segments 35-T thereof are positioned for release out through distal opening 403. FIGS. 7A-B are a plan view and an end view of a distal portion of tool 400 including an alternate embodiment outer member 730 (in lieu of outer member 430), in which a slot 73-S is formed in a sidewall 732 of outer member 730. Sidewall 732, similar to sidewall 432 of outer member 430, defines a lumen 735 of outer member 730, in which inner member 420 is slideably engaged, and which has a distal portion sized to contain device 1200 in a similar fashion to that described above for lumen 435 of outer member 430 (FIG. 4A). FIG. 7A illustrates slot 73-S extending proximally from an open end thereof, which coincides with a distal opening 703 of lumen 735. FIGS. 7A-B illustrate leadlet 120 passing laterally out through slot 73-S, when tip segments 35-T of tines 303 are positioned in proximity to distal opening 703, for example, after ventricular portion 100 has been deployed. According to the illustrated embodiment, slot 73-S allows leadlet 120 to move laterally away from tines 303 of atrial portion 200 prior to the deployment of atrial portion 200 out through distal opening 703, for example, to prevent leadlet 120 from becoming trapped against tissue at the implant site when tines 303 are released from spring loading for engagement with the tissue.

Device 1200 may be loaded into outer member 730 in a similar fashion to that described above for loading device 1200 into outer member 430. But, with further reference to FIG. 7B, it may be appreciated that care must be taken when drawing atrial portion 200 into lumen 735 through distal opening 703, to load device 1200 into outer member 730, so that none of tines 303 catch in slot 73-S, and so free distal end 352 of each tine tip segment 35-T rests against a location on an inner surface 72 of sidewall 732 that is circumferentially offset from slot 73-S.

Figure 8D:
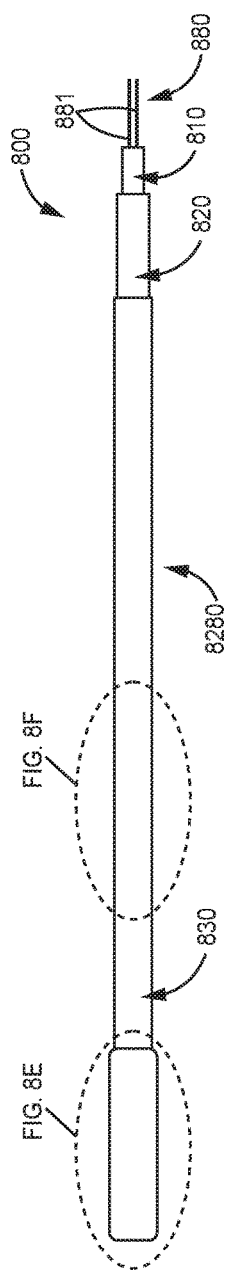
FIG. 8D is a plan view of the system of FIG. 8A, according to some embodiments.
Figure 8E:
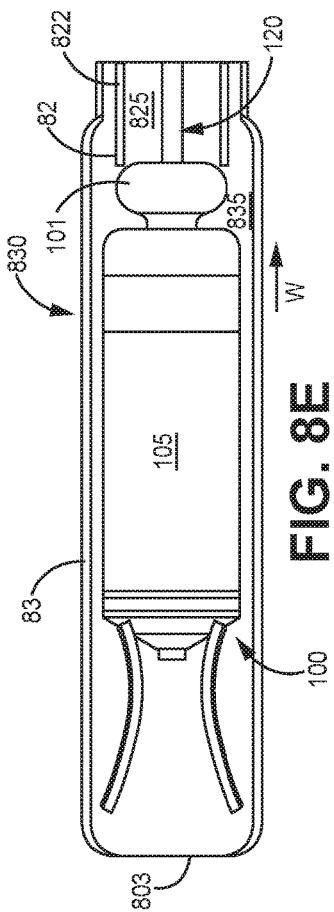
FIGS. 8E-F are longitudinal cross-section views through portions of the system, the general locations of which are indicated in FIG. 8D, according to some embodiments.
Figure 8F:
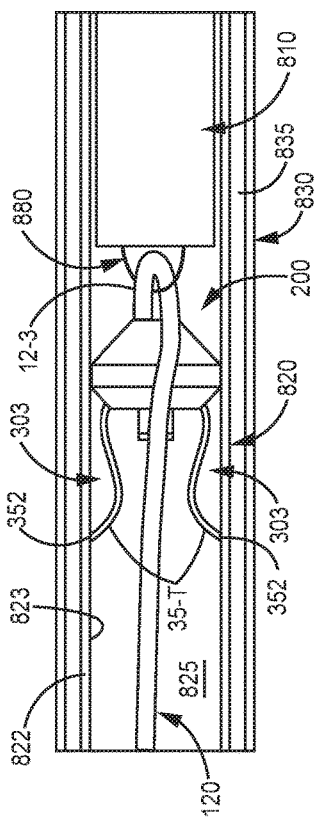

According to some alternate embodiments, atrial portion 200 of device 1200 may be downsized relative to ventricular portion 100 of device 1200, and included with delivery tool 800 in a system 8280, portions of which are shown in FIGS. 8A-F. FIG. 8A illustrates such a device 1200 prior to loading into delivery tool 800; and FIGS. 8D-F illustrate system 8280 with device 1200 loaded in delivery tool 800. Delivery tool 800 includes an elongate outer member 830 and an inner assembly 850. Inner assembly 850, which is slideably engaged within a lumen 835 of outer member 830 (FIGS. 8D-F), is shown protruding distally from a distal opening 803 of lumen 835 in FIG. 8A. FIG. 8A further illustrates inner assembly 850 including an elongate inner member 820, an elongate sheath 810, which is slideably engaged within lumen 825 of inner member 820, and a tether 880, which is engaged with leadlet 120 of device 1200, being looped thereabout. According to the illustrated embodiment, sheath 810 includes side-by-side longitudinally extending lumens 815 that have openings located at a distal-facing surface 81 of sheath 810, and opposing lengths of tether 880 extend within lumens 815 of sheath 810 to form the loop that engages leadlet 120 in proximity to distal-facing surface 81; and proximal ends 881 of these tether lengths, which may be seen in FIG. 8D, protrude from a proximal port opening of delivery tool 800 where an operator may grasp them. With further reference to FIG. 8A, in conjunction with FIG. 2A, leadlet 120 is folded over on itself along third segment 12-3 for engagement with the loop of tether 880, for example, such that the bend thereof that is engaged by the tether loop is spaced about one inch apart from first end 201 of atrial portion core 250. According to the illustrated embodiment, tether 880 together with sheath 810 may be employed to pull atrial portion 200 of device 1200, per arrow Q, into lumen 825 of inner member 820 so that atrial portion 200 is contained in lumen 825 and tines 303 of atrial portion 200 are spring-loaded, as shown in FIG. 8F, with free distal ends 352 of tip segments 35-T resting against an inner surface 823 of a sidewall 822 of inner member 820 that defines lumen 825. Subsequently, after sheath 810 has been pulled proximally within lumen 825 of inner member 820, until leadlet 120 is contained therein and a distal end 82 of inner member 820 abuts proximal end 101 of ventricular portion housing 105, outer member 830 may be advanced relative to inner assembly 850 so that a distal end 83 of outer member 830 contains ventricular portion 100 of device 1200, as shown in FIG. 8E. It should be noted that tether 880 and sheath 810 may be in the form of any suitable snare-type tool, known to those skilled in the art.

FIG. 8A further illustrates sidewall 822 of inner member 820 having a slot 82-S formed therein along distal end 82 thereof, wherein slot 82-S extends proximally from an open end thereof, which coincides with a distal opening 802 of lumen 825. Slot 82-S, similar to slot 73-S described above for outer member 730, allows leadlet 120 to move laterally away from tines 303 of atrial portion 200 prior to the deployment of atrial portion 200 out through distal opening 802, for example, to prevent leadlet 120 from becoming trapped against tissue at the implant site when tines 303 are released from spring loading for engagement with the tissue. The deployment of atrial portion 200, according to some methods, is described below in conjunction with FIG. 9B.

It may be appreciated that care must be taken, when drawing atrial portion 200 into lumen 825 through distal opening 803, so that none of tines 303 catch in slot 73-S. Thus, with reference to FIG. 8B, which is an end view of inner assembly 850, an orientation guide for atrial portion 200 may be included in inner assembly 850. FIG. 8B illustrates the loop of tether 880 spanning lumens 815 and extending over a groove 811, which is formed in distal-facing surface 81 of sheath 810 as the orientation guide. According to the illustrated embodiment, groove 811 is sized to receive third segment 12-3 of leadlet 120, so that, by positioning folded third segment 12-3 in groove 811, the operator can orient atrial portion 200 with tines 303 circumferentially offset from slot 82-S, when pulling atrial portion 200 into distal end 82 of inner member 820. (The resulting position of tines is shown with dashed lines in FIG. 8B.) In some embodiments, an outer surface of sheath 810 may interlock with inner surface 823 of inner member 820, for example, via an optional interlocking spline configuration shown in the exemplary cross-section of FIG. 8C, to keep sheath 810 and member 820 in a predetermined circumferential orientation with respect to one another, for example, the orientation shown in FIG. 8B.

Figure 9A:
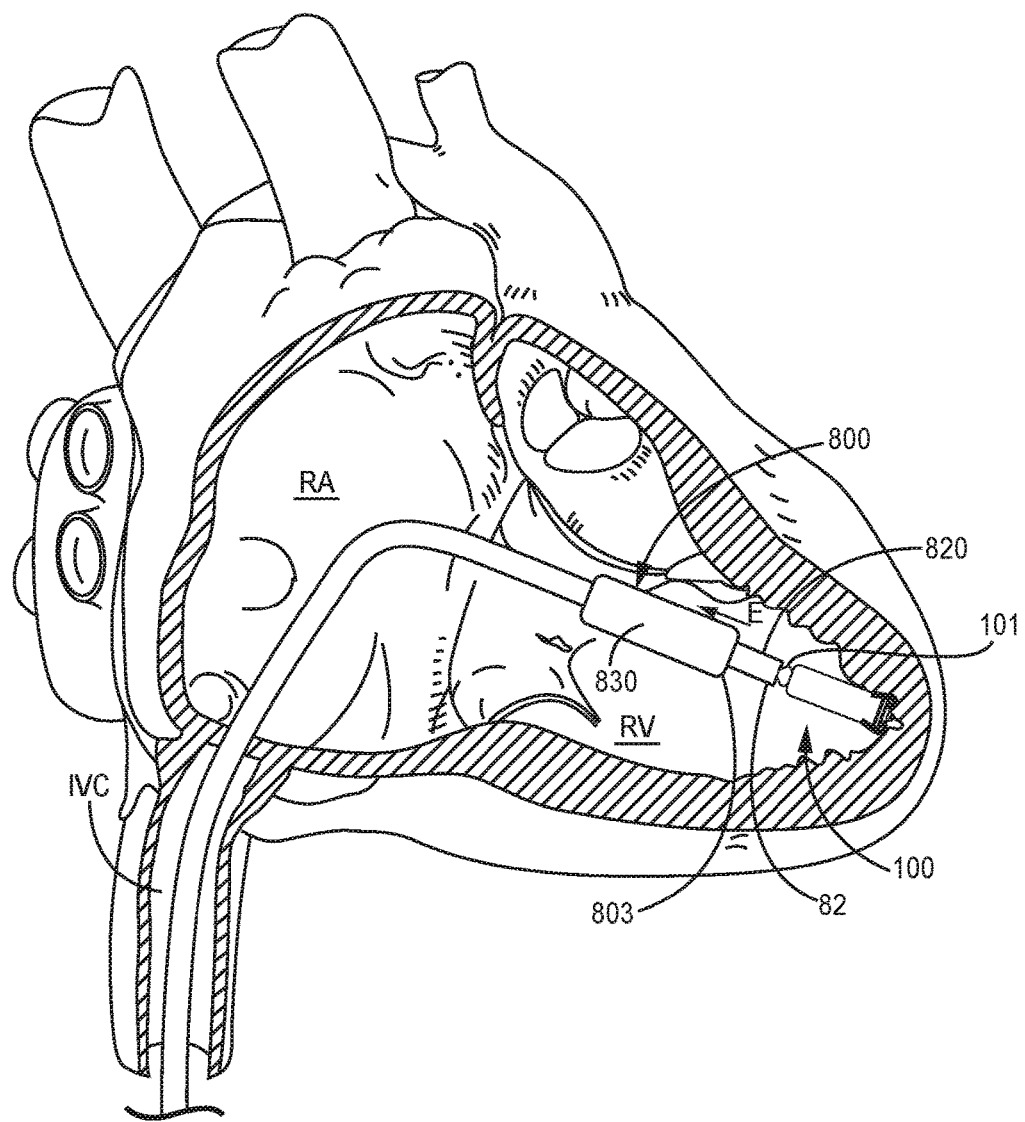
FIG. 9A is a schematic diagram of the system of FIGS. 8A-E advanced into a right ventricle for deployment of a ventricular portion of the device of FIG. 2A, according to some methods.
Figure 9B:
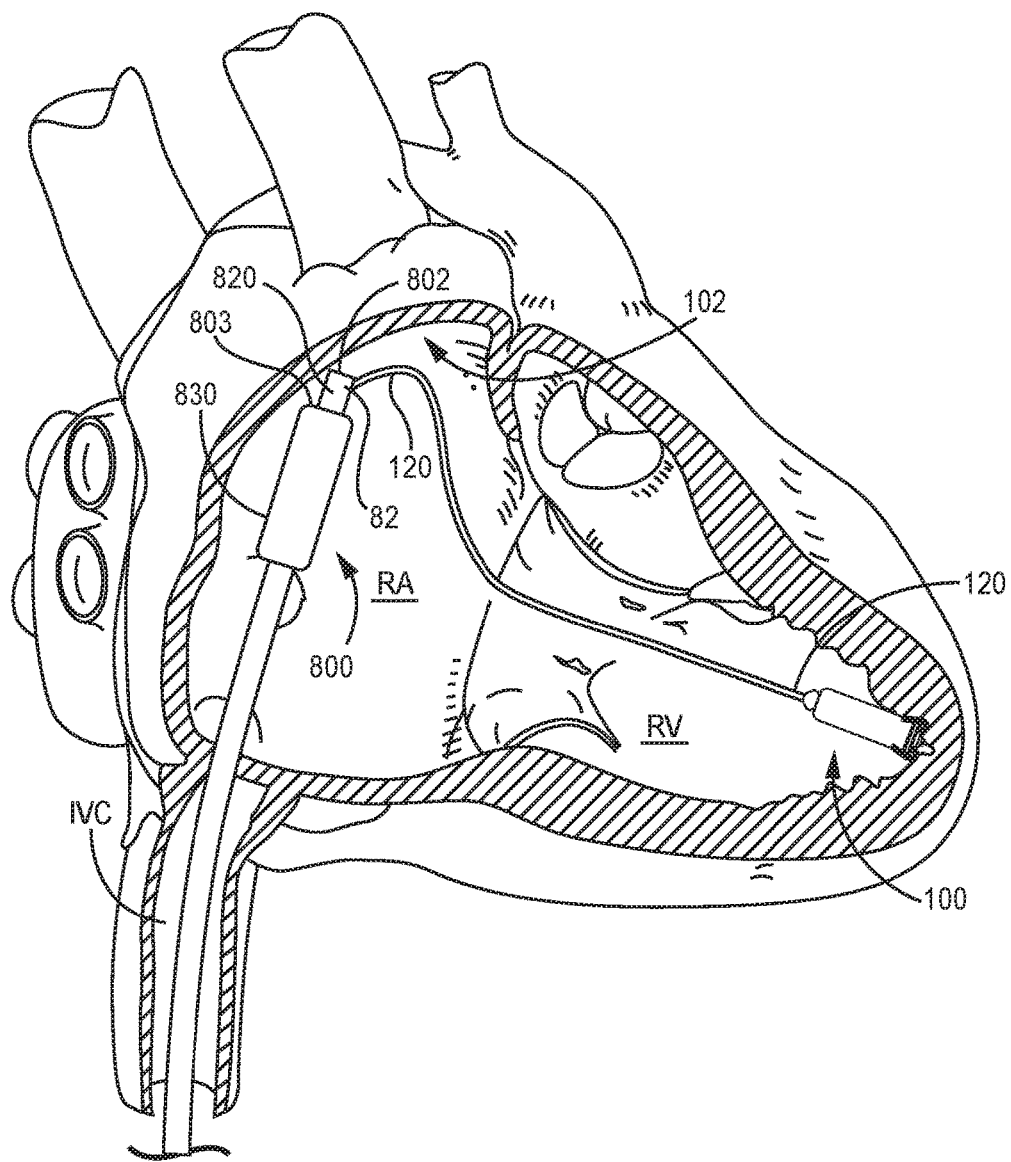
FIG. 9B is a schematic diagram of a delivery tool of the system positioned in a right atrium for deployment of the atrial portion of the device, according to some methods.
Figure 9C:
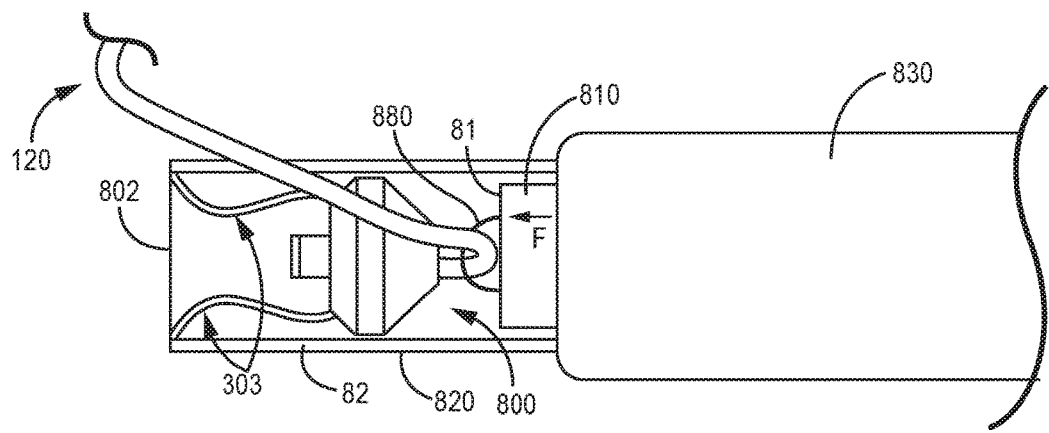
FIG. 9C is a plan view, with a partial cut-away section, of a portion of the interventional medical system of FIGS. 8A-E, according to some embodiments.

With further reference to FIG. 8D, general relative locations of ventricular portion 100 and atrial portion 200 are indicated when device 1200 is loaded into delivery tool 800 for deployment, for example, being spaced about 15 cm to 20 cm apart from one another, which corresponds to the aforementioned exemplary length of flexible leadlet 120. FIGS. 9A-C outline some exemplary methods for deploying device 1200 from delivery tool 800. Like tool 400, described above, tool 800 may have a length of approximately 110 cm to reach into right ventricle RV. Furthermore, delivery tool 800 may include articulating features to facilitate the navigation thereof as described below. For example, outer member 830 may include a pull-wire assembly integrated therein, according to construction features known to those skilled in the art.

FIG. 9A is a schematic diagram of delivery tool 800 positioned within right ventricle RV, after the operator has deployed ventricular portion 100. According to some methods, the operator deploys ventricular portion 100 by advancing tool 800 through a venous system of the patient, for example, from a femoral venous access site and up through an inferior vena cava IVC of the patient into right atrium RA and across the tricuspid valve into right ventricle RV, until distal opening 803 of delivery tool 800 abuts the target implant site. With distal opening 803 abutting the implant site, the operator applies a push force through tool 800 while retracting outer member 830 relative to inner assembly 850 and device 1200 (arrow W of FIG. 8E), to release fixation tines 103 of ventricular portion 100 out through distal opening 803 for engagement with tissue at the implant site, as shown in FIG. 9A. With reference back to FIG. 8E, the abutment of inner member distal end 82 against ventricular portion proximal end 101 applies pressure to stabilize ventricular portion 100 as the operator retracts outer member 830. Once ventricular portion 100 is deployed, the operator may withdraw outer member 830 and inner member 820, relative to sheath 810 and tethered device 1200, back up into right atrium RA (arrow E of FIG. 9A) in order to deploy atrial portion 200.

FIG. 9B is a schematic diagram of delivery tool 800 positioned in right atrium RA for deployment of device atrial portion 200. FIG. 9B illustrates distal end 82 of inner member 820 still protruding distally from distal opening 803 of outer member 830 and directed into atrial appendage 102, where the operator will abut distal end 82 against pectinate muscle PM (FIG. 2B) for deployment of atrial portion 200 at a target implant site. FIG. 9B further illustrates a length of leadlet 120 that has passed out from inner member 820 as the operator withdrew outer member 830 and inner member 820 into right atrium RA. With reference to the cross-section view in FIG. 9C, atrial portion 200 and distal-facing surface 81 of sheath 810 also became located in closer proximity to distal opening 802 of inner member 820, as the operator withdrew outer member 830 and inner member 820 into right atrium RA. With distal opening 802 of inner member 820 abutting pectinate muscle PM, the operator may apply a push force to atrial portion 200, through sheath 810, per arrow F, to release the spring loading of fixation tines 303 for engagement with pectinate muscle PM at the implant site, as shown in FIG. 2B. (Note that FIGS. 6A-F, and the corresponding description thereof, may also pertain to the release of tines 303 from inner member 820.) FIG. 9C further illustrates leadlet 120 extending laterally away from atrial portion 200, as allowed by slot 82-S (FIG. 8A), when atrial portion 200 is positioned for deployment; thus, leadlet 120 will not become trapped against tissue at the implant site, when tines 303 are released from spring loading for engagement with the tissue.

Figure 10A:
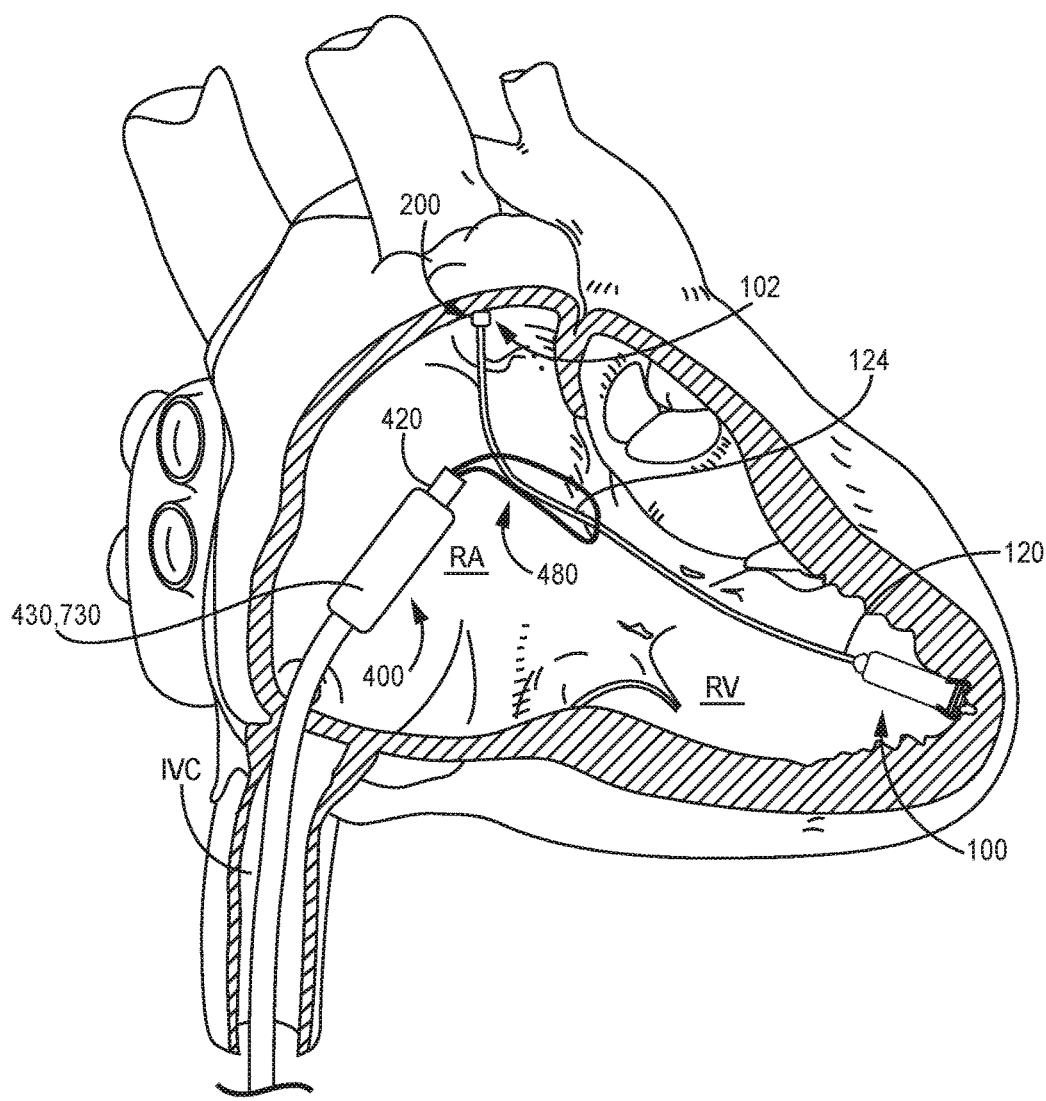
FIG. 10A is a schematic diagram related to some retrieval methods with a delivery tool described in conjunction with FIGS. 4A-B.
Figure 10B:
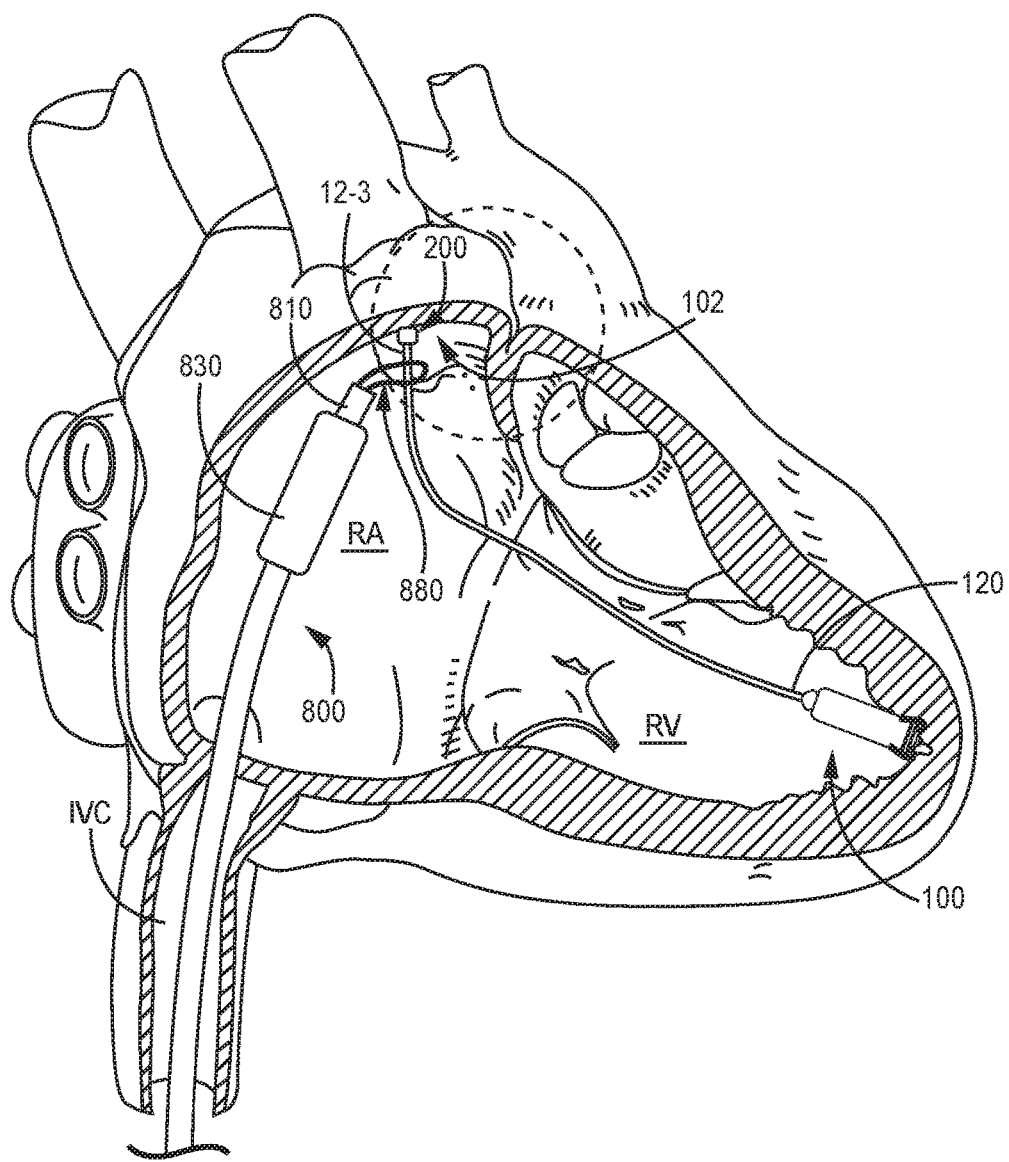
FIG. 10B is a schematic diagram related to some retrieval methods with the delivery tool described in conjunction with FIGS. 8A-F.

Once ventricular portion 100 and atrial portion 200 of device 1200 are both deployed at respective implant sites, by any of the above-described delivery tools 400, 800, tether 480, 880 may be released from leadlet 120 of device 1200, for example, by pulling one of tether ends 481, 881 proximally from the corresponding lumen 425, 815, to unloop tether 480, 880. However, before unlooping tether 480, 880, if the operator determines that device 120 needs to be retrieved, for example, for repositioning, tether 480, 880 may be employed to disengage, and reload into tool 400, 800, atrial portion 200 followed by ventricular portion 100 of device 1200. FIGS. 10A-B are schematic diagrams related to some retrieval methods. FIG. 10A shows delivery tool 400 positioned relative to flexible leadlet 120 and the loop of tether 480 advanced distally out from inner member 420 to cinch around leadlet 120, preferably at the aforementioned zone 124 (FIG. 2A) so that, in retrieving device, leadlet 120 can be folded at the same location at which it was initially folded for loading, as described above in conjunction with FIGS. 2A and 4A. According to some preferred embodiments, a radiopaque marker may be coupled to leadlet 120 at zone 124 so the operator can locate zone 124 under fluoroscopy. FIG. 10B shows delivery tool 800 positioned relative to flexible leadlet 120, and the loop of tether 880 advanced out from sheath 810 to cinch around leadlet 120 along third segment 12-3, for example, at the preferred location described above for loading atrial portion 200 into delivery tool 800, about one inch away from atrial portion core 250.

Figure 11:
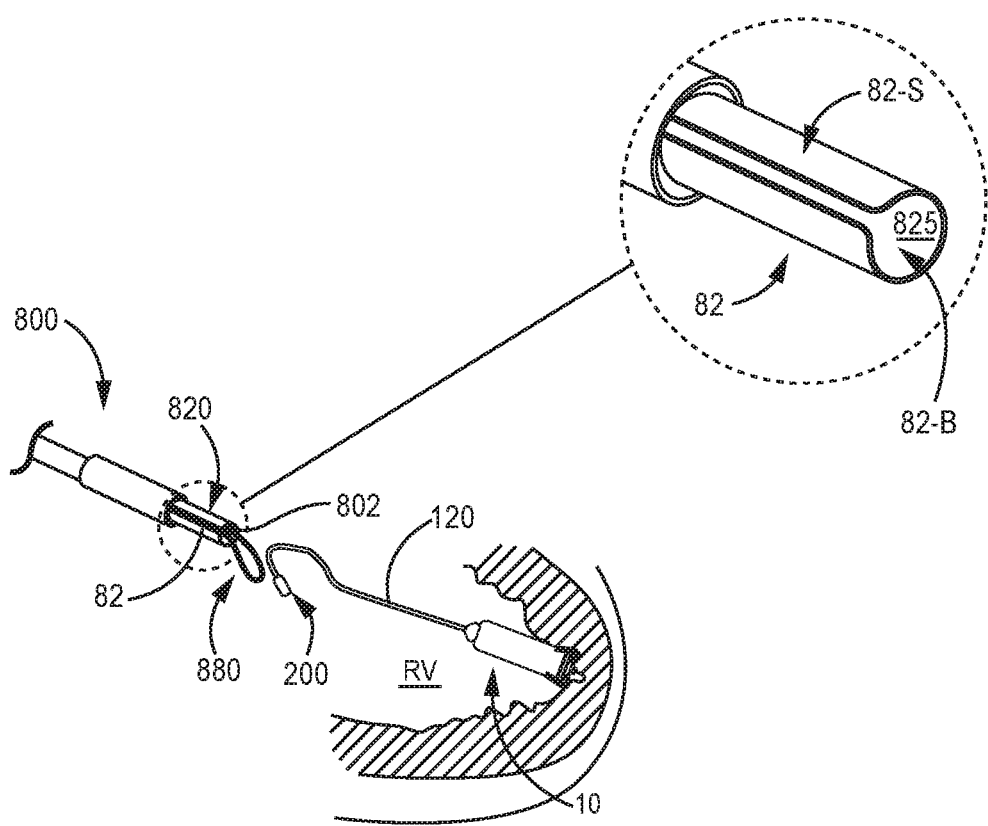
FIG. 11 is a schematic diagram related to an alternate deployment method.

Finally, in some alternative methods, an operator may choose to initially load device 1200 into a delivery tool, for example, tool 800 described above, so that the orientation of the loaded ventricular and atrial portions 100, 200 are as shown in FIG. 2A, without flexible leadlet 120 being folded over on itself, and without tines 303 of atrial portion 200 being spring-loaded in the delivery tool. If so, after deploying ventricular portion 100 to the implant site in right ventricle RV, as shown in FIG. 9A, the operator can retract an entirety of delivery tool 800, per arrow E, until atrial portion 200 exits distal opening 802 of inner member 820. Then, the operator may advance sheath 810 with respect to inner member 820 until tether 880 extends out from distal opening 802, as shown in FIG. 11, and maneuver tether 880 to loop around leadlet 120 in proximity to atrial portion 200. Once tether 880 is secured around leadlet 120, the operator may pull, per arrow Q (FIG. 8A), atrial portion 200 into lumen 825 of inner member 820 so that tines 303 are spring-loaded, as shown in FIG. 9C, and then position tool 800 in right atrium RA to deploy atrial portion 200 at the target implant site, for example, in the same manner as was described above in conjunction with FIG. 9B. With further reference to FIG. 11, an enlarged perspective view of inner member distal end 82 is shown, wherein, according to some embodiments, distal end 82 is terminated by a beveled edge 82-B, for example, to facilitate the passage of leadlet 120 into slot 82-S when the operator pulls atrial portion 200 into lumen 825.

In the foregoing detailed description, specific exemplary embodiments have been described. However, it may be appreciated that various modifications and changes can be made without departing from the scope of the invention as set forth below.

We claim:

1. A tissue penetrating fixation component for an implantable medical device, the component comprising:
    a base defining a longitudinal axis of the component and being configured to be fixedly attached to the device so that a perimeter of the component extends around an electrode of the device, and so that the longitudinal axis of the component is generally aligned along a longitudinal axis of the device, the base including at least one inward bending segment defining a groove extending parallel to the longitudinal axis of the component, the inward bending segment being directed toward the axis; and
    a plurality of tines extending from the base and being spaced apart from one another around a perimeter thereof such that each of the at least one inward bending segment of the base is located between adjacent pairs of tines.

2. The component of claim 1, wherein each tine comprises:
    a proximal, spring portion being fixedly attached to the base and having a spring-biased pre-formed curvature, the pre-formed curvature, in proximity to the base, extending in a first direction, generally parallel to the axis of the component, and then sweeping laterally, outward from the axis; and
    a distal portion including a proximal section, a hook section, and tip section terminated by a rounded free distal end, the proximal section extending from the proximal, spring portion and being pre-formed to extend in a second direction and along a relatively straight line to the hook section, the proximal section being oriented, by the spring-biased pre-formed curvature of the proximal, spring portion, so that the second direction is generally opposite the first direction, and the relatively straight line intersects the axis at an acute angle of between about 30 degrees and about 50 degrees, the hook section having a deformable pre-formed curvature that extends from the proximal section back toward the axis of the component, the tip section being pre-formed to extend along a relatively straight line from the hook section to the rounded free distal end, and the tip section being oriented, by the pre-formed curvature of the hook section, when un-deformed, to extend toward the axis of the component, such that the tip section and the proximal section enclose an angle in a range from about 90 degrees to about 120 degrees; and
    wherein, when the device, having the fixation component fixedly attached thereto, is loaded within a tubular sidewall of a delivery tool, so that the rounded free distal end of each tine of the component engages an inner surface of the sidewall, to hold the proximal, spring portion of each tine of the component in a spring-loaded condition, each tip section of the distal portion extends away from the axis of the component at an acute angle in a range from about 45 degrees to about 75 degrees for deployment of the corresponding rounded free distal end out from the tool tubular sidewall; and
    upon deployment of the rounded free distal end of each tine, the tip section of each distal portion rotates away from the axis to an angle that approaches 90 degrees, relative to the axis, in response to an initial release of the spring-loaded condition of the corresponding proximal, spring portion.

3. The component of claim 1, wherein the base and the plurality of tines are integrally formed.

4. The component of claim 1, wherein the base and the plurality of tines are formed from a medical grade superelastic metal.

5. The component of claim 1, wherein the base and the plurality of tines are integrally formed from medical grade Nitinol tubing.

6. The component of claim 1, wherein each tine comprises:
    a proximal, spring portion being fixedly attached to the base and having a spring-biased pre-formed curvature, the pre-formed curvature, in proximity to the base, extending in a first direction, generally parallel to the axis of the component, and then sweeping laterally, outward from the axis; and
    a distal portion including a proximal section, a hook section, and tip section terminated by a rounded free distal end, the proximal section extending from the proximal, spring portion and being pre-formed to extend in a second direction and along a first relatively straight line to the hook section, the proximal section being oriented, by the spring-biased pre-formed curvature of the proximal, spring portion, so that the second direction is generally opposite the first direction, the hook section having a deformable pre-formed curvature that extends from the proximal section back toward the axis of the component, the tip section being pre-formed to extend along a second relatively straight line from the hook section to the rounded free distal end, and the tip section being oriented, by the pre-formed curvature of the hook section, when un-deformed, to extend toward the axis of the component.

7. The component of claim 6, wherein the first relatively straight line intersects the axis at an acute angle of between about 30 degrees and about 50 degrees.

8. The component of claim 6, wherein the tip section and the proximal section enclose an angle in a range from about 90 degrees to about 120 degrees.

9. The component of claim 6, wherein, when the device, having the fixation component fixedly attached thereto, is loaded within a tubular sidewall of a delivery tool, so that the rounded free distal end of each tine of the component engages an inner surface of the sidewall, to hold the proximal, spring portion of each tine of the component in a spring-loaded condition, each tip section of the distal portion extends away from the axis of the component at an acute angle for deployment of the corresponding rounded free distal end out from the tool tubular sidewall.

10. The component of claim 9, wherein the acute angle is in a range from about 45 degrees to about 75 degrees.

11. The component of claim 9, wherein, upon deployment of the rounded free distal end of each tine, the tip section of each distal portion rotates away from the axis to an angle that approaches 90 degrees, relative to the axis, in response to an initial release of the spring-loaded condition of the corresponding proximal, spring portion.

12. The component of claim 9, wherein the groove of the inward bending segment is sized to receive a leadlet of the device.

* * * * *